(12) United States Patent
Dunman et al.

(10) Patent No.: US 9,517,230 B2
(45) Date of Patent: Dec. 13, 2016

(54) SMALL MOLECULE RNASE INHIBITORS AND METHODS OF USE

(71) Applicants: UNIVERSITY OF ROCHESTER, Rochester, NY (US); BOARD OF REGENTS OF THE UNIVERSITY OF NEBRASKA, Lincoln, NE (US); TEMPLE UNIVERSITY—OF THE COMMONWEALTH SYSTEM OF HIGHER EDUCATION, Philadelphia, PA (US)

(72) Inventors: Paul M. Dunman, Pittsford, NY (US); Patrick D. Olson, St. Louis, MO (US); Wayne Childers, New Hope, PA (US)

(73) Assignees: UNIVERSITY OF ROCHESTER, Rochester, NY (US); BOARD OF REGENTS OF THE UNIVERSITY OF NEBRASKA, Lincoln, NE (US); TEMPLE UNIVERSITY—OF THE COMMONWEALTH SYSTEM OF HIGHER EDUCATION, Philadelphia, PA (US)

(*) Notice: Subject to any disclaimer, the term of this patent is extended or adjusted under 35 U.S.C. 154(b) by 0 days.

(21) Appl. No.: 14/744,205

(22) Filed: Jun. 19, 2015

(65) Prior Publication Data
US 2015/0283118 A1 Oct. 8, 2015

Related U.S. Application Data

(62) Division of application No. 13/981,011, filed as application No. PCT/US2012/022724 on Jan. 26, 2012, now Pat. No. 9,089,545.

(60) Provisional application No. 61/436,342, filed on Jan. 26, 2011.

(51) Int. Cl.
| | |
|---|---|
| A61K 31/427 | (2006.01) |
| C07D 307/68 | (2006.01) |
| C07D 307/56 | (2006.01) |
| C07D 405/06 | (2006.01) |
| C07D 417/06 | (2006.01) |
| A61K 31/341 | (2006.01) |
| A61K 45/06 | (2006.01) |
| A61K 31/402 | (2006.01) |
| C07D 207/337 | (2006.01) |
| C12Q 1/44 | (2006.01) |

(52) U.S. Cl.
CPC ......... *A61K 31/427* (2013.01); *A61K 31/341* (2013.01); *A61K 31/402* (2013.01); *A61K 45/06* (2013.01); *C07D 207/337* (2013.01); *C07D 307/56* (2013.01); *C07D 307/68* (2013.01); *C07D 405/06* (2013.01); *C07D 417/06* (2013.01); *C12Q 1/44* (2013.01); *G01N 2333/922* (2013.01); *G01N 2500/04* (2013.01); *G01N 2500/10* (2013.01)

(58) Field of Classification Search
CPC .................................................... A61K 31/427
See application file for complete search history.

(56) References Cited

U.S. PATENT DOCUMENTS

| | | | |
|---|---|---|---|
| 6,936,432 B2 | 8/2005 | Gopalan et al. | |
| 2002/0052396 A1* | 5/2002 | Bailey et al. | 514/369 |
| 2002/0123077 A1 | 9/2002 | O'Toole et al. | |
| 2003/0134904 A1 | 7/2003 | Giordano et al. | |
| 2004/0176277 A1 | 9/2004 | Sowadski et al. | |
| 2004/0180889 A1 | 9/2004 | Suto et al. | |
| 2005/0042674 A9 | 2/2005 | Yu et al. | |
| 2005/0187409 A1 | 8/2005 | Powers et al. | |
| 2008/0033025 A1* | 2/2008 | Pellecchia | A61K 31/427 |
| | | | 514/369 |
| 2008/0090825 A1 | 4/2008 | Chikauchi et al. | |
| 2009/0163545 A1 | 6/2009 | Goldfarb | |
| 2013/0303585 A1 | 11/2013 | Dunman et al. | |

FOREIGN PATENT DOCUMENTS

| | | |
|---|---|---|
| DE | 264918 | 2/1989 |
| GB | 2386892 A * | 10/2003 |
| JP | H3182742 | 8/1991 |
| WO | WO 2005020990 A1 * | 3/2005 |
| WO | 2010003533 | 1/2010 |
| WO | 2012/103295 A1 | 8/2012 |

OTHER PUBLICATIONS

Stedman's Online Medical Dictionary, Entry for microbe, obtained from http://www.stedmansonline.com/content/mlrM0900000753 on Aug. 9, 2015.*
Mayo Clinic, Staph Infections—Prevention, obtained from http://www.mayoclinic.org/diseases-conditions/staph-infections/basics/prevention/con-20031418 on Aug. 9, 2015.*
Graham, B.S., "Clinical trials of HIV vaccines." HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM. pp. I-20-I-38.*
Machine translation of International Application Publication No. WO 2005/020990 by Leonetti et al., obtained from espacenet on Aug. 10, 2015.*
Andre et al. Journal of Antimicrobial Chemotherapy 2006, 57, 245-251.*

(Continued)

*Primary Examiner* — Matthew Coughlin
(74) *Attorney, Agent, or Firm* — Kilpatrick Townsend & Stockton, LLP

(57) ABSTRACT

Small molecule inhibitors of bacterial ribonuclease (e.g., RnpA) and methods for their synthesis and use are described herein. The methods of using the compounds include treating and preventing microbial infections and inhibiting bacterial ribonuclease.

10 Claims, 7 Drawing Sheets

(56) References Cited

OTHER PUBLICATIONS

Olson et al. (2011) Small Molecule Inhibitors of Staphylococcus aureus RnpA Alter Cellular mRNA Turnover, Exhibit Antimicrobial Activity, and Attenuate Pathogenesis. PLoS Pathog 7(2): e1001287.*
Suree et al. Bioorg. Med. Chem. 2009, 17, 7174-7185.*
Xiong et al. Arch. Microbiol. 2009, 191, 879-884.*
Chinese Patent Application No. 201280015124.6, Office Action mailed Oct. 28, 2015, 7 pages.
Japanese Patent Application No. 2013-551335, Office Action mailed Nov. 18, 2015, 12 pages.
Pubchem CID 1268985, retrieved from http://pubchem.ncbi.nlm.nih.gov/summary/summary.cgi?cid= 1268985 on Apr. 17, 2012.
International Search Report for PCT/US2012/022724, mailed Jul. 6, 2012.
International Preliminary Report on Patentability for PCT/US2012/022724, mailed Aug. 8, 2013.
Akaike, T. (1974) A new look at the statistical model identification, IEE Trans. Automat. Contr. 19, 716-723.
Altschul, S.F., et al., Basic local alignment search tool. J Mol Biol, 1990. 215(3): p. 403-10.
Anderson KL, Roberts C, Disz T, Vonstein V, Hwang K, et al. (2006) Characterization of the Staphylococcus aureus heat-shock, cold-shock, stringent, and SOS responses and their effects on log-phase mRNA turnover. J Bacteriol 188: 6739-6756.
Anderson KL, Dunman PM (2009) Messenger RNA Turnover Processes in Escherichia coli, Bacillus subtilis, and Emerging Studies in Staphylococcus aureus. Int J Microbiol 2009: 525491.
Appelbaum PC (2007) Reduced glycopeptide susceptibility in methicillin-resistant Staphylococcus aureus (MRSA). Int J Antimicrob Agents 30: 398-408.
Arraiano, C. M., Andrade, J. M., Domingues, S., Guinote, I. B., Malecki, M., Matos, R. G., Moreira, R. N., Pobre, V., Reis, F. P., Saramago, M., Silva, I. J., and Viegas, S. C. (2010) The critical role of RNA processing and degradation in the control of gene expression, FEMS Microbiol Rev 34, 883-923.
Bancroft EA (2007) Antimicrobial resistance: it's not just for hospitals. Jama 298: 1803-1804.
Bae, T., et al., Staphylococcus aureus virulence genes identified by bursa aurealis mutagenesis and nematode killing. Proc Natl Acad Sci U S A, 2004. 101(33): p. 12312-7. Epub Aug 10, 2004.
Beenken KE, Dunman PM, McAleese F, Macapagal D, Murphy E, et al. (2004) Global Gene Expression in Staphylococcus aureus Biofilms J Bacteriol 186: 4665-4684.
Broad Institute, Luminescence Microorganism-Based Dose Confirmation HTS to Identify Compounds Cytotoxic to SK(-)GAS Group A Streptococcus, PubChem BioAssay AID 1900, Deposit Date Aug. 14, 2009, access date Mar. 13, 2015, obtained from http://pubchem.ncbi.nlm.nih.gov/assay/assay.cgi?aid=1900.
Carpousis AJ (2007) The RNA degradosome of Escherichia coli: an mRNA-degrading machine assembled on RNase E. Annu Rev Microbiol 61: 71-87.
Charpentier E, Anton AL, Barry P, Alfonso B, Fang Y, et al. (2004) Novel cassette-based shuttle vector system for gram-positive bacteria. Appl Environ Microbiol 70: 6076-6085.
Chaudhuri RR, Allen AG, Owen PJ, Shalom G, Stone K, et al. (2009) Comprehensive identification of essential Staphylococcus aureus genes using Transposon-Mediated Differential Hybridisation (TMDH). BMC Genomics 10: 291.
Cherbuliez, E., Marszalek, J., and Rabinowitz, J. (1964) Etude de structures peptidiques a l'aide de phenylisothiocyanate VI. Sur la recation de quelques acides amines et de quelques thiols avec le phenylisothiocyanate, Helv. Chem. Acta 47, 1666-1672.
Cierny, G., 3rd. (2011) Surgical treatment of osteomyelitis, Plast Reconstr Surg 127 Suppl 1, 190S-204S.
Commichau FM, Rothe FM, Herzberg C, Wagner E, Hellwig D, et al. (2009) Novel activities of glycolytic enzymes in Bacillus subtilis: interactions with essential proteins involved in mRNA processing. Mol Cell Proteomics 8: 1350-1360.

Condon C (2003) RNA processing and degradation in Bacillus subtilis. Microbiol Mol Biol Rev 67: 157-174, table of contents.
Dunman, P.M., et al., Uses of Staphylococcus aureus GeneChips in genotyping and genetic composition analysis J Clin Microbiol, 2004. 42(9): p. 4275-83.
Even S, Pellegrini O, Zig L, Labas V, Vinh J, et al. (2005) Ribonucleases J1 and J2: two novel endoribonucleases in B. subtilis with functional homology to E. coli RNase E. Nucleic Acids Res 33: 2141-2152. Print 2005.
Frank DN, Pace NR (1998) Ribonuclease P: unity and diversity in a tRNA processing ribozyme. Annu Rev Biochem 67: 153-180.
Gossringer M, Kretschmer-Kazemi Far R, Hartmann RK (2006) Analysis of RNase P protein (rnpA) expression in Bacillus subtilis utilizing strains with suppressible rnpA expression. J Bacteriol 188: 6816-6823.
Guerrier-Takada C, Gardiner K, Marsh T, Pace N, Altman S (1983) The RNA moiety of ribonuclease P is the catalytic subunit of the enzyme. Cell 35: 849-857.
Hartmann RK, Gossringer M, Spath B, Fischer S, Marchfelder A (2009) The making of tRNAs and more—RNase P and tRNase Z. Prog Mol Biol Transl Sci 85: 319-368.
He et al., "Scaling up of continuous-flow, microwave-assisted, organic reactions by varying the size of Pd-functionalized catalytic monoliths," Beilstein J. Org. Chem., 7:1150-1157 (2011).
Hidalgo, I. J., Raub, T. J., and Borchardt, R. T. (1989) Characterization of the human colon carcinoma cell line (Caco-2) as a model system for intestinal epithelial permeability, Gastroenterology 96, 736-749.
Huntzinger E, Boisset S, Saveanu C, Benito Y, Geissmann T, et al. (2005) Staphylococcus aureus RNAIII and the endoribonuclease III coordinately regulate spa gene expression. EMBO J 24: 824-835. Epub 2005.
Jendralla et al., Synthesis and biological activity of new HMG-CoA reductase inhibitors. 2. Derivatives of 7-(1H-pyrrol-3-yl)-substituted-3,5-dihydroxyhept-6(E)-enoic (-heptanoic) acids, J. Med. Chem. 33(1): 61-70 (1990).
Ji Y, Zhang B, Van SF, Horn, Warren P, et al. (2001) Identification of critical staphylococcal genes using conditional phenotypes generated by antisense RNA. Science 293: 2266-2269.
Jia et al., Synthesis of 1-phenoxyacetyl-4-aroylthiosemicarbazides, Huaxue Tongbao 1:38-40 (1994).
Jiang, X., A. Diwa, and J.G. Belasco, Regions of RNase E important for 5'-end-dependent RNA cleavage and autoregulated synthesis. J Bacteriol, 2000. 182(9): p. 2468-75.
Kansy, M., Senner, F., and Gubernator, K. (1998) Physicochemical high throughput screening: parallel artificial membrane permeation assay in the description of passive absorption processes, J Med Chem 41, 1007-1010.
Kazantsev AV, Pace NR (2006) Bacterial RNase P: a new view of an ancient enzyme. Nat Rev Microbiol 4: 729-740.
Khan et al., Condensed benzopyrans. IV. Synthesis of some derivatives of 7H- and 9H-pyrano[3,2-E]indoles. Journal of Heterocyclic Chemistry, 16(5): 997-999 (1979).
Klevens RM, Morrison MA, Nadle J, Petit S, Gershman K, et al. (2007) Invasive methicillin-resistant Staphylococcus aureus infections in the United States. Jama 298: 1763-1771.
Kobayashi K, Ehrlich SD, Albertini A, Amati G, Andersen KK, et al. (2003) Essential Bacillus subtilis genes. Proc Natl Acad Sci U S A 100: 4678-4683.
Kochansky, C. J., McMasters, D. R., Lu, P., Koeplinger, K. A., Kerr, H. H., Shou, M., and Korzekwa, K. R. (2008) Impact of pH on plasma protein binding in equilibrium dialysis, Mol Pharm 5, 438-448.
Kole R, Baer MF, Stark BC, Altman S (1980) E. coli RNAase P has a required RNA component. Cell 19: 881-887.
Lehnik-Habrink M, Pfortner H, Rempeters L, Pietack N, Herzberg C, et al. (2010) The RNA degradosome in Bacillus subtilis: identification of CshA as the major RNA helicase in the multiprotein complex. Mol Microbiol 21: 21.
Letunic I, Copley RR, Pils B, Pinkert S, Schultz J, et al. (2006) Smart 5: domains in the context of genomes and networks. Nucleic Acids Res 34: D257-260.

(56) References Cited

OTHER PUBLICATIONS

Lew, D. P., and Waldvogel, F. A. (2004) Osteomyelitis, *Lancet* 364, 369-379.
Lewis, K. (2008) Multidrug tolerance of biofilms and persister cells, Curr Top Microbiol Immunol 322, 107-131.
Li, Z., X. Wang, and Y. Da, Synthesis of 2-(5-(2-chlorophenyl)2-furoylamido)-5-aryloxymethyl-1,3,4-thiadiazoles under microwave irradiation. Synthetic Communications, 2001. 31: p. 1829-1836.
Liu F, Altman S (1994) Differential evolution of substrates for an RNA enzyme in the presence and absence of its protein cofactor. Cell 77: 1093-1100.
Lundblad EW, Xiao G, Ko JH, Altman S (2008) Rapid selection of accessible and cleavable sites in RNA by *Escherichia coli* RNase P and random external guide sequences. Proc Natl Acad Sci USA 105: 2354-2357.
Mackie GA (1998) Ribonuclease E is a 5'-end-dependent endonuclease. Nature 395: 720-723.
Mader U, Zig L, Kretschmer J, Homuth G, Putzer H (2008) mRNA processing by RNases J1 and J2 affects *Bacillus subtilis* gene expression on a global scale. Mol Microbiol 70: 183-196.
Manetti et al, Ligand-Based Virtual Screening, Parallel Solution-Phase and Microwave-Assisted Synthesis as Tools to Identify and Synthesize New Inhibitors of *Mycobacterium tuberculosis*, ChemMedChem, 1(9): 973-989 (2006).
Marvin MC, Engelke DR (2009) Broadening the mission of an RNA enzyme. J Cell Biochem 108: 1244-1251.
Mathy N, Benard L, Pellegrini O, Daou R, Wen T, et al. (2007) 5'-to-3' exoribonuclease activity in bacteria: role of RNase J1 in rRNA maturation and 5' stability of mRNA. Cell 129: 681-692.
McDougal LK, Steward CD, Killgore GE, Chaitram JM, McAllister SK, et al. (2003) Pulsed-field gel electrophoresis typing of oxacillin-resistant *Staphylococcus aureus* isolates from the United States: establishing a national database. J Clin Microbiol 41: 5113-5120.
McMasters, D. R., Torres, R. A., Crathern, S. J., Dooney, D. L., Nachbar, R. B., Sheridan, R. P., and Korzekwa, K. R. (2007) Inhibition of recombinant cytochrome P450 isoforms 2D6 and 2C9 by diverse drug-like molecules, J Med Chem 50, 3205-3213.
PubChem CID 5031694, retrieved from the Internet: < URL: http://pubchem.ncbi.nlm.nih.gov/summary/summary.cgi?cid=5031694> [retrieved on Jun. 23, 2012], Sep. 18, 2005.
Database registry, Chemical abstracts service, Columbus, Ohio, US, XP002724925, Database accession No. 940113-01-9, Jun. 29, 2007.
Database registry, Chemical abstracts service, Columbus, Ohio, US, XP002724926, Database accession No. 940112-35-6, Jun. 29, 2007.
Chinese Patent Application No. 201280015222.X, Office Action dated Sep. 26, 2014.
Chinese Patent Application No. 201280015124.6, Office Action mailed Sep. 26, 2014.
Chinese Patent Application No. 201280015124.6, Office Action mailed May 19, 2015, and English Translation, 8 pages.
U.S. Appl. No. 13/981,015, Office Action mailed Oct. 16, 2014.
U.S. Appl. No. 13/981,015, Final Office Action mailed Feb. 3, 2015 (10 pages).
U.S. Appl. No. 13/981,011, Notice of Allowance mailed Mar. 20, 2015, 30 pages.
Esnault, et al., "Pin1 Modulates the Type 1 Immune Response", PLoS One 2(2):e226 (2007).
European Application No. 12738820.5, Extended European Search Report Received mailed on Jul. 11, 2014, 12 pages.
European Application No. 12739832.9, Extended European Search Report mailed on Jun. 26, 2014, 12 pages.
International Application No. PCT/US2012/022662, International Preliminary Report on Patentability mailed on Jul. 30, 2013, 9 pages.
International Application No. PCT/US2012/022662, International Search Report mailed on Jul. 17, 2012, 4 pages.
Li et al., Synthesis of 1-Aryloxyacetyl-4-(5-(4-Chlorophenyl)--2-Furoyl) Semicarbazides, Jan. 1, 2001, pp. 1433-1440.

Miczak, A., et al., Proteins associated with RNase E in a multicomponent ribonucleolytic complex. Proc Natl Acad Sci U S A, 1996. 93(9): p. 3865-9.
Mosmann, T. (1983) Rapid colorimetric assay for cellular growth and survival: application to proliferation and cytotoxicity assays, J Immunol Methods 65, 55-63.
Novick RP (2003) Autoinduction and signal transduction in the regulation of staphylococcal virulence. Mol Microbiol 48: 1429-1449.
Olson, P. D., Kuechenmeister, L. J., Anderson, K. L., Daily, S., Beenken, K. E., Roux, C. M., Reniere, M. L., Lewis, T. L., Weiss, W. J., Pulse, M., Nguyen, P., Simecka, J. W., Morrison, J. M., Sayood, K., Asojo, O. A., Smeltzer, M. S., Skaar, E. P., and Dunman, P. M. (2011) Small molecule inhibitors of *Staphylococcus aureus* RnpA alter cellular mRNA turnover, exhibit antimicrobial activity, and attenuate pathogenesis, PLoS Pathog 7, e1001287.
Rao, N., Ziran, B. H., and Lipsky, B. A. (2011) Treating osteomyelitis: antibiotics and surgery, Plast Reconstr Surg 127 Suppl 1, 177S-187S.
Rauhut, R., and Klug, G. (1999) mRNA degradation in bacteria, FEMS Microbiol Rev 23, 353-370.
Renneberg, J. and M. Walder, A mouse model for simultaneous pharmacokinetic and efficacy studies of antibiotics at sites of infection. J Antimicrob Chemother, 1988. 22(1): p. 51-60.
Rice, L. B. (2008) Federal funding for the study of antimicrobial resistance in nosocomial pathogens: no ESKAPE, J Infect Dis 197, 1079-1081.
Roberts C, Anderson KL, Murphy E, Projan SJ, Mounts W, et al. (2006) Characterizing the Effect of the *Staphylococcus aureus* Virulence Factor Regulator, SarA, on Log-Phase mRNA Half-Lives. J Bacteriol 188: 2593-2603.
Roux et al., Characterization of components of the *Staphylococcus aureus* mRNA degradosome holoenzyme-like complex, Journal of Bacteriology, vol. 193, No. 19, Oct. 1, 2011, pp. 5520-5526.
Sahu, J., Meher, S., and Nayak, A. (1985) Studies on thiazolidinones. Part XV. Synthesis of thiazolidinones from mono- and disubstituted thioureas and heterocyclic substituents, J. Ind. Chem. Soc. 62, 71-73.
Sankawa, U. and S. Shibata, Biosynthesis of natural products. IV. Biosynthesis of itaconitin. 1. Degradation studies on itaconitin. Chem Pharm Bull (Tokyo), 1969. 17(10): p. 2020-4.
Schedl P, Primakoff P (1973) Mutants of *Escherichia coli* thermosensitive for the synthesis of transfer RNA. Proc Natl Acad Sci U S A 70: 2091-2095.
Schepetkin et al., Novel Small-Molecule Inhibitors of Anthrax Lethal Factor Identified by High-Throughput Screening, Journal of Medicinal Chemistry, vol. 49, No. 17, Aug. 2006, pp. 5232-5244.
Schepetkin et al., Novel Small-Molecule Inhibitors of Anthrax Lethal Factor Identified by High-Throughput Screening—Supporting Information, Journal of Medicinal Chemistry, vol. 49, No. 17, Aug. 2006, pp. S1-S10.
Schultz J, Milpetz F, Bork P, Ponting CP (1998) SMART, a simple modular architecture research tool: identification of signaling domains. Proc Natl Acad Sci USA 95: 5857-5864.
Selles, P., Synthesis and biological evaluation of himanimide C and unnatural analogues. Org Lett, 2005. 7(4): p. 605-8.
Shahbabian K, Jamalli A, Zig L, Putzer H (2009) RNase Y, a novel endoribonuclease, initiates riboswitch turnover in *Bacillus subtilis*. EMBO J 28: 3523-3533.
Shorr AF, Tabak YP, Killian AD, Gupta V, Liu LZ, et al. (2006) Healthcare-associated bloodstream infection: A distinct entity? Insights from a large U.S. database. Crit Care Med 34: 2588-2595.
Simchen, G., and Seigl, G. (1992) Synthese von derivaten der a-ketocarbonsauren aus 2-O-funktionell substituierten trimethylsilykeyenacetalen, Libigs Ann. Chem., 607-613.
Spitzfaden C, Nicholson N, Jones JJ, Guth S, Lehr R, et al. (2000) The structure of ribonuclease P protein from *Staphylococcus aureus* reveals a unique binding site for single-stranded RNA. J Mol Biol 295: 105-115.
Takayama K, Kjelleberg S (2000) The role of RNA stability during bacterial stress responses and starvation Environ Microbiol 2: 355-365.

(56) References Cited

OTHER PUBLICATIONS

Tian, X. J., Yang, X. W., Yang, X., and Wang, K. (2009) Studies of intestinal permeability of 36 flavonoids using Caco-2 cell monolayer model, Int J Pharm 367, 58-64.

Vanzo NF, Li YS, Py B, Blum E, Higgins CF, et al. (1998) Ribonuclease E organizes the protein interactions in the *Escherichia coli* RNA degradosome. Genes Dev 12: 2770-2781.

Walker SC, Engelke DR (2006) Ribonuclease P: the evolution of an ancient RNA enzyme. Crit Rev Biochem Mol Biol 41: 77-102.

Wang et al., Expeditious One-Step Method to 5-Aryl-2-furoyl Substituted Thioureas and Thiosemicarbazides in Aqueous Media, Synthetic Communications, vol. 36, No. 7, XP55119842, ISSN: 0039-7911, DOI: 10.1080/00397910500464244, Mar. 1, 2006, pp. 843-847.

Wang et al., Microwave Induced Synthesis of 2-(2-Furoylamid0)-5-Aryloxymethyl-1,3,4-Thiadiazoles, Synthetic Communications, vol. 31, No. 16, XP55119851, ISSN: 0039-7911, DOI: 10.1081/SCC-100105133, Jan. 1, 2011, pp. 2537-2541.

Waugh DS, Pace NR (1990) Complementation of an RNase P RNA (*rnpB*) gene deletion in *Escherichia coli* by homologous genes from distantly related eubacteria. J Bacteriol 172: 6316-6322.

Weiss EC, Spencer HJ, Daily SJ, Weiss BD, Smeltzer MS (2009) Impact of *sarA* on antibiotic susceptibility of *Staphylococcus aureus* in a catheter-associated in vitro model of biofilm formation. Antimicrob Agents Chemother 53: 2475-2482.

Weiss, E. C., Zielinska, A., Beenken, K. E., Spencer, H. J., Daily, S. J., and Smeltzer, M. S. (2009) Impact of sarA on daptomycin susceptibility of *Staphylococcus aureus* biofilms in vivo, Antimicrob Agents Chemother 53, 4096-4102.

Wohnsland, F., and Faller, B. (2001) High-throughput permeability pH profile and high-throughput alkane/water log P with artificial membranes, J Med Chem 44, 923-930.

Yao S, Sharp JS, Bechhofer DH (2009) Bacillus subtilis RNase J1 endonuclease and 5' exonuclease activities in the turnover of DeltaermC mRNA. Rna 15: 2331-2339.

Yang, J., Jamei, M., Yeo, K. R., Rostami-Hodjegan, A., and Tucker, G. T. (2007) Misuse of the well-stirred model of hepatic drug clearance, Drug Metab Dispos 35, 501-502.

Zetola N, Francis JS, Nuermberger EL, Bishai WR (2005) Community-acquired methicillin-resistant *Staphylococcus aureus*: an emerging threat. Lancet Infect Dis 5: 275-286.

Zhang, W.J., et al., Impact of azaproline on amide cis-trans isomerism: conformational analyses and NMR studies of model peptides including TRH analogues. J Am Chem Soc, 2003. 125(5): p. 1221-35.

Australian Patent Application No. 2012211253, Patent Examination Report No. 1 mailed Mar. 16, 2016, 5 pages.

Japanese Patent Application No. 2013-551335, Decision of Rejection mailed May 9, 2016, 4 pages.

Chinese Patent Application No. 201280015124.6, Fourth Office Action mailed Jul. 5, 2016, 6 pages with translation.

\* cited by examiner

SMALL MOLECULE RNASE INHIBITORS AND METHODS OF USE

CROSS-REFERENCE TO PRIORITY APPLICATIONS

This patent application is a divisional application of U.S. application Ser. No. 13/981,011, filed Jul. 22, 2013, which is a U.S. national stage application under 35 U.S.C. §371 of PCT/US2012/022724, filed Jan. 26, 2012, which claims priority to U.S. Provisional Application No. 61/436,342, filed Jan. 26, 2011. These applications are incorporated herein by reference in their entireties.

FIELD

The subject matter disclosed herein generally relates to small molecule inhibitors of bacterial ribonuclease (RNase) and methods of their preparation. Also, the subject matter described herein generally relates to methods of using the small molecule inhibitors described herein to treat and prevent microbial infections.

BACKGROUND

*Staphylococcus aureus* infections are often associated with high rates of morbidity and mortality (see Shorr et al., *Crit Care Med*, 34: 2588-2595 (2006)). Indeed, reports estimate that in 2005 the organism caused more U.S. deaths than HIV/AIDS (see Bancroft, E. A., *Jama*, 298: 1803-1804 (2007); Klevens et al., *Jama*, 298: 1763-1771 (2007)). The emergence of vancomycin-resistant, methicillin-resistant, multidrug-resistant, and hypervirulent strains has further accentuated the need for novel antibiotics (see Appelbaum, P. C., *Int J Antimicrob Agents*, 30: 398-408 (2007); Zetola et al., *Lancet Infect Dis*, 5: 275-286 (2005)). Bacterial RNA processing and degradation are required cellular processes that can be exploited for antimicrobial drug discovery.

Much of the understanding of bacterial RNA degradation comes from studies of *Escherichia coli* where bulk mRNA decay is thought to be catalyzed by a holoenzyme complex (RNA degradosome), which consists of at least four subunits: RNase E (me), RNA helicase (rhlB), enolase (eno), and PNPase (pnpA) (see Carpousis, A. J., *Annu Rev Microbiol*, 61: 71-87 (2007)). RNase E is an essential ribonuclease and a key component of the degradosome complex. It serves as a scaffold for the assembly of other members of the RNA degradosome and catalyzes the initial endoribonucleolytic event during substrate degradation (see Mackie, G. A., *Nature*, 395: 720-723 (1998); Vanzo et al., *Genes Dev*, 12: 2770-2781 (1998)). Based on its essentiality, RNase E could be considered an appropriate target for antibiotic drug discovery. However, many Gram-positive bacteria, including *S. aureus*, lack an RNase E amino acid ortholog (see Condon, C., *Microbiol Mol Biol Rev*, 67: 157-174 (2003)). As a consequence, their degradation components and mechanism(s) of mRNA decay are less understood.

Recent studies suggest that at least two ribonucleases, RNase J1 and RNase Y, contribute to bulk mRNA degradation within *Bacillus subtilis*, and presumably other Gram-positive bacteria. *B. subtilis* ribonuclease J1 is a bifunctional ribonuclease, with 5' exonuclease and endonuclease activities, that mediates mRNA degradation in vitro (see Even et al., *Nucleic Acids Res*, 33: 2141-2152 (2005); Mathy et al., *Cell*, 129: 681-692 (2007)). The enzyme has also been found to interact with enolase (a component of the *E. coli* RNA degradosome) and RNase J1 depleted *B. subtilis* strains demonstrate a moderate decrease in mRNA decay, suggesting that it may be the functional equivalent to *E. coli* RNase E (see Even et al., *Nucleic Acids Res*, 33: 2141-2152 (2005); Commichau et al., *Mol Cell Proteomics*, 8: 1350-1360 (2009); Mader et al., *Mol Microbiol*, 70: 183-196 (2008)). However, mRNA turnover still occurs in RNase J1 diminished cells and RNA species containing 5' strong-hairpin structures are not effectively degraded by the enzyme, indicating that additional factors are likely to contribute to *B. subtilis* cellular RNA degradation (see Yao et al., *Rna*, 15: 2331-2339 (2009)). Ribonuclease Y is a recently identified endonuclease that may ostensibly work in concert with RNase J1 to mediate bulk RNA decay. RNase Y can cleave mRNA molecules containing high-order secondary structures and globally affects cellular messenger RNA turnover (see Shahbabian et al., *Embo J*, 28: 3523-3533 (2009)). Both RNase J1 and RNase Y are essential enzymes and, in that regard, could be considered targets for antimicrobial drug discovery (see Kobayashi et al., *Proc Natl Acad Sci USA*, 100: 4678-4683 (2003)). However, it remains to be seen whether RNase J1, RNase Y, and/or previously uncharacterized ribonucleases modulate mRNA decay within *S. aureus*.

SUMMARY

In accordance with the purposes of the disclosed materials, compounds, compositions, kits, and methods, as embodied and broadly described herein, the disclosed subject matter relates to compositions, methods of making said compositions, and methods of using said compositions. More specifically, compounds and compositions for use as inhibitors of bacterial ribonuclease (RNase) are provided herein. A class of RNase inhibitors includes compounds of the following formula:

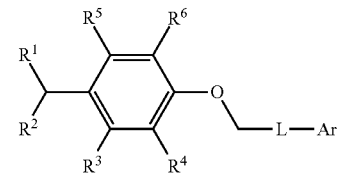

and pharmaceutically acceptable salts and prodrugs thereof. In these compounds, Ar is a substituted or unsubstituted aryl or substituted or unsubstituted heteroaryl; L is

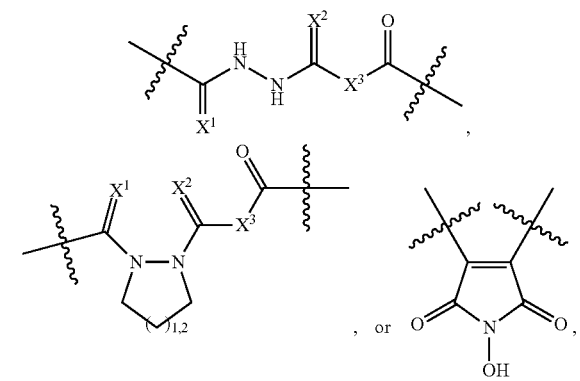

wherein $X^1$ and $X^2$ are each independently O or S, and wherein $X^3$ is $CH_2$ or NH; and $R^1$, $R^2$, $R^3$, $R^4$, $R^5$, and $R^6$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl. In this class of compounds, if $R^1$ and $R^2$ are methyl, $R^3$, $R^4$, $R^5$, and $R^6$ are hydrogen, and Ar is unsubstituted furan, then L is not

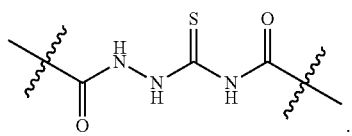 [SMILES: *C(=O)NNC(=S)NC(*)=O]

A class of RNase inhibitors includes compounds of the following structure: compound of the following structure:

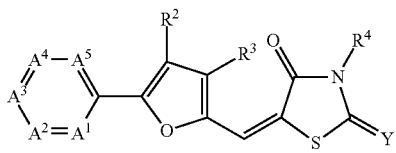

and pharmaceutically acceptable salts and prodrugs thereof. In these compounds, $A^1$, $A^2$, $A^3$, $A^4$, and $A^5$ are each independently selected from N and $CR^1$; $R^1$, $R^2$, and $R^3$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl; $R^4$ and $R^5$ are each independently selected from hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, or substituted or unsubstituted heteroalkyl; and Y is O, S, or $NR^5$. In this class of compounds, if $A^1$, $A^2$, $A^4$, and $A^5$ are CH, $R^2$ and $R^3$ are hydrogen, $A^3$ is CCl, and Y is S, then $R^4$ is not $-CH_2CH_2CO_2H$.

Also provided herein are compositions including one or more compounds as described above and a pharmaceutically acceptable carrier.

Further provided herein are methods of treating or preventing a microbial infection in a subject. In some embodiments, the methods comprise administering to the subject an effective amount of an RNase inhibitor of the following structure:

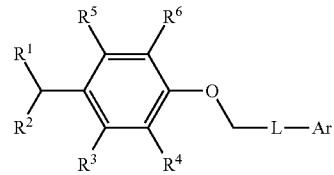

or pharmaceutically acceptable salts or prodrugs thereof. In these compounds, Ar is a substituted or unsubstituted aryl or substituted or unsubstituted heteroaryl; L is

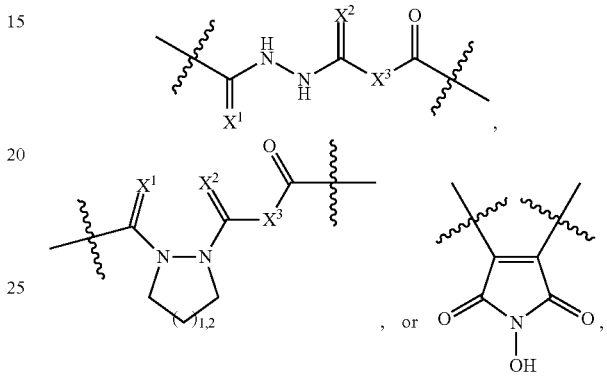

wherein $X^1$ and $X^2$ are each independently O or S, and wherein $X^3$ is $CH_2$ or NH; and $R^1$, $R^2$, $R^3$, $R^4$, $R^5$, and $R^6$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl. Optionally, Ar can be selected from the group consisting of substituted or unsubstituted furan, substituted or unsubstituted thiophene, or substituted or unsubstituted phenyl. In some examples, the RNase inhibitor is

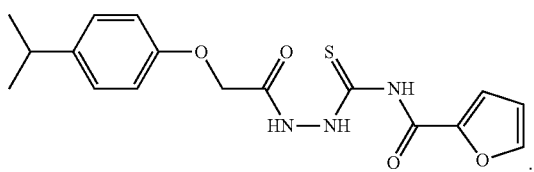 [SMILES: CC(C)c1ccc(OCC(=O)NNC(=S)NC(=O)c2ccco2)cc1]

In other embodiments, the method of treating or preventing a microbial infection in a subject comprises administering to the subject an effective amount of an RNase inhibitor of the following structure:

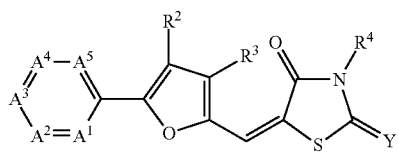

or a pharmaceutically acceptable salt or prodrug thereof. In these compounds, $A^1$, $A^2$, $A^3$, $A^4$, and $A^5$ are each independently selected from N and $CR^1$; $R^1$, $R^2$, and $R^3$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl; $R^4$ and $R^5$ are each independently selected from hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, or substituted or unsubstituted heteroalkyl; and Y is O, S, or $NR^5$. In some examples, the RNase inhibitor is

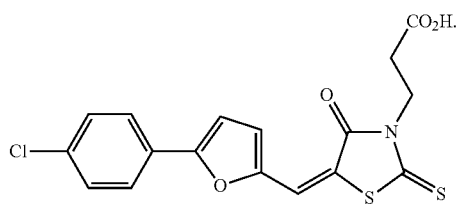 [SMILES: O=C(O)CCN1C(=O)/C(=C\c2ccc(-c3ccc(Cl)cc3)o2)SC1=S]

In some embodiments, the microbial infection is a bacterial infection. The bacterial infection can be, for example, a Gram positive bacterial infection. Optionally, the bacterial infection is a *Staphylococcus* infection such as, for example, a *Staphylococcus aureus* infection. The *Staphylococcus aureus* infection can be a drug-resistant *Staphylococcus aureus* infection or a biofilm-associated *Staphylococcus aureus* infection. In some examples, the RNase inhibitor is a RnpA inhibitor. Optionally, the methods can further comprise administering a second compound to the subject, wherein the second compound is an antibacterial compound.

Also provided herein are methods of inhibiting a bacterial ribonuclease comprising contacting the bacterial ribonuclease with an effective amount of an RNase inhibitor. In some embodiments, the RNase inhibitor is a compound of the following structure:

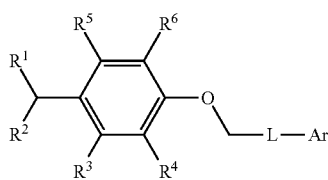

or pharmaceutically acceptable salts or prodrugs thereof. In these compounds, Ar is a substituted or unsubstituted aryl or substituted or unsubstituted heteroaryl; L is

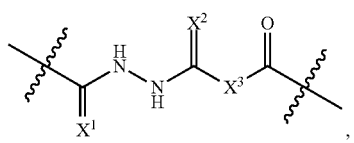

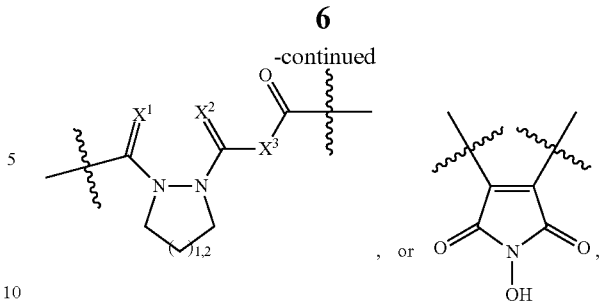

wherein $X^1$ and $X^2$ are each independently O or S, and wherein $X^3$ is $CH_2$ or NH; and $R^1$, $R^2$, $R^3$, $R^4$, $R^5$, and $R^6$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl.

In other embodiments, the RNase inhibitor is a compound of the following structure:

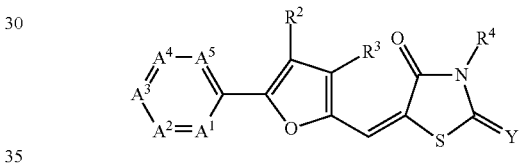

or a pharmaceutically acceptable salt or prodrug thereof. In these compounds, $A^1$, $A^2$, $A^3$, $A^4$, and $A^5$ are each independently selected from N and $CR^1$; $R^1$, $R^2$, and $R^3$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl; $R^4$ and $R^5$ are each independently selected from hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, or substituted or unsubstituted heteroalkyl; and Y is O, S, or $NR^5$.

Optionally, the bacterial ribonuclease is the protein component of *Staphylococcus aureus* RNase P (e.g., RnpA). The contacting can occur, for example, in vivo or in vitro.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 2A is an SDS-PAGE of purified recombinant *S. aureus* RnpA; shown are molecular markers (Lanes M), 2.5 μg and 25 μg elution products (Lanes 1 and 2, respectively). FIG. 2B depicts the gel-mobility of 1 μg of total *S. aureus* RNA following 60 min incubation in the absence (−) or presence (+) of 50 pmol of each putative ribonuclease (indicated) in 1× reaction buffer (2 mM NaCl, 2 mM $MgCl_2$, 50 mM Tris-HCl, pH 6.0). FIG. 2C displays the mobility of 0.5 pmol in vitro transcribed spa mRNA following 60 min incubation in the absence (0 pmol) or presence of the indicated amount of RnpA protein in 1× reaction buffer. Molecular weight markers (M) are shown. FIG. 2D shows reverse-transcription mediated PCR products of 2 μg of in vitro transcribed spa mRNA in the absence (−) or presence (+) of 50 pmol RnpA or RNase J1 and in the absence (serum alone) or presence of 1, 2.5, 5, 10, or 20 μg RnpA polyclonal antibody. FIG. 2E shows plotted measurements for all mRNA species measured on a GeneChip at 0 (X-axis) and 10 min (Y-axis) post-transcriptional arrest. Grey dashed line indicates the lower limit of sensitivity for each sample.

DETAILED DESCRIPTION

Figure 1:
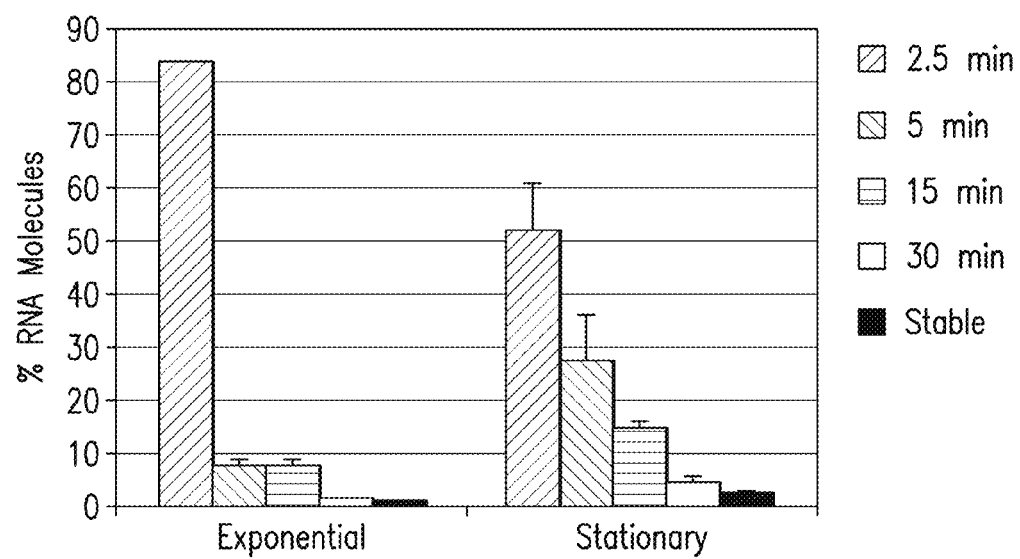
FIG. 1 is a graph showing the percent of detectable mRNA species (Y-axis) with a half life of ≤2.5, 5, 15, 30, or >30 min during exponential- and/or stationary-phase growth (X-axis).

Provided herein are small molecule inhibitors of bacterial RnpA associated ribonuclease (RNase) activity, methods of their preparation, and methods of their use in treating and preventing microbial infections. The small molecule inhibitors exploit a novel mechanism of treating microbial infections, such as *Staphylococcus aureus*, which involves the essential *S. aureus* protein, RnpA, catalyzing rRNA and mRNA digestion. This mechanism has not previously been known or developed. Exploiting this activity, high throughput and secondary screening assays were employed to identify small molecule inhibitors of RnpA-mediated RNA degradation. These agents limited cellular mRNA degradation and exhibited antimicrobial activity against several microbes, including predominant methicillin-resistant *S. aureus* (MRSA) lineages circulating throughout the U.S., vancomycin intermediate susceptible *S. aureus* (VISA), vancomycin resistant *S. aureus* (VRSA) and other Gram-positive bacterial pathogens with high RnpA amino acid conservation (see McDougal et al., *J Clin Microbiol*, 41: 5113-5120 (2003)). As provided herein, the RnpA-inhibitors limit disease in a systemic mouse infection model and have antimicrobial activity against biofilm-associated *S. aureus*. Taken together, these findings indicate that RnpA plays a role in *S. aureus* RNA degradation, demonstrate that high through-put screening can be used to identify mRNA turnover inhibitors, and provide proof of principle for RNA catabolism-based antimicrobial therapy.

The materials, compounds, compositions, articles, and methods described herein may be understood more readily by reference to the following detailed description of specific aspects of the disclosed subject matter and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., bacterial infection). It is understood that this is typically in relation to some standard or expected value, in other words it is relative, but that it is not always necessary for the standard or relative value to be referred to. For example, "reduces bacterial infection" means reducing the spread of a bacterial infection relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

By "antimicrobial" is meant the ability to treat or control (e.g., reduce, prevent, inhibit, or eliminate) the growth of a microbe at any concentration. Similarly, the term "antibacterial" refers to the ability to treat or control cellular bacteria growth at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —OZ$^1$ where Z$^1$ is alkyl as defined above.

The term "alkenyl" as used herein is a hydrocarbon group of from 2 to 24 carbon atoms with a structural formula containing at least one carbon-carbon double bond. Asymmetric structures such as (Z$^1$Z$^2$)C=C(Z$^3$Z$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O.

The terms "amine" or "amino" as used herein are represented by the formula —NZ$^1$Z$^2$, where Z$^1$ and Z$^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)Z$^1$ or —C(O)OZ$^1$, where Z$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula Z$^1$OZ$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula Z$^1$C(O)Z$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —SiZ$^1$Z$^2$Z$^3$, where Z$^1$, Z$^2$, and Z$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$Z$^1$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples.

Compounds

Small molecule inhibitors of bacterial ribonuclease (RNase) are described herein. A first group of inhibitors includes compounds represented by Formula I:

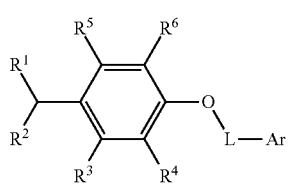

(I)

and pharmaceutically acceptable salts and prodrugs thereof.

In Formula I, Ar is a substituted or unsubstituted aryl or substituted or unsubstituted heteroaryl. In some examples, Ar is substituted or unsubstituted furan, substituted or unsubstituted thiophene, or substituted or unsubstituted phenyl.

Also in Formula I, L is

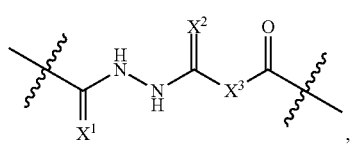

-continued

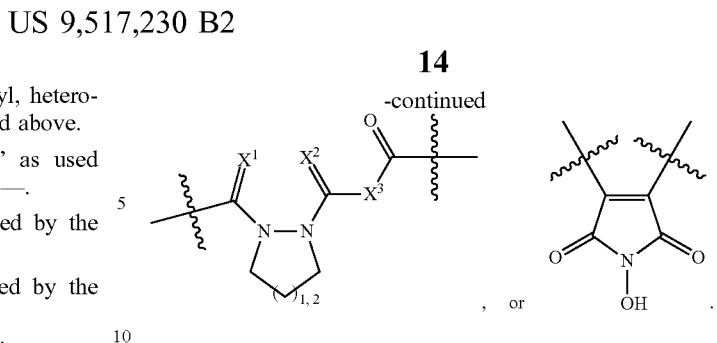

$X^1$ and $X^2$ can each independently be O or S. In some examples, $X^1$ is O and $X^2$ is S. $X^3$ can be CH$_2$ or NH. In L, ⁓ signifies the attachment of the carbon atom to Ar or —CH$_2$O— in Formula I. For example, compounds according to Formula I can be represented by the following structures based on L:

Structure I-A

Structure I-B

Structure I-C

In some examples of Structure I-A, $X^1$ and $X^2$ can be O and $X^3$ can be NH.

Additionally in Formula I, $R^1$, $R^2$, $R^3$, $R^4$, $R^5$, and $R^6$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl. In some examples, $R^1$ and $R^2$ are methyl. In some examples, $R^3$, $R^4$, $R^5$, and $R^6$ are hydrogen.

In Formula I, adjacent R groups, e.g., $R^1$ and $R^2$; $R^3$ and $R^4$; and $R^5$ and $R^6$, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. For example, $R^5$ can be a substituted or unsubstituted ethylene group and $R^6$ can be a substituted or unsubstituted propylene group that combine to form a substituted or unsubstituted phenyl. Other adjacent R groups include the combinations of $R^1$ and $R^2$ and $R^3$ and $R^4$.

As described above, Ar in Formula I can be furan. These embodiments of Formula I can include the following Structure I-D:

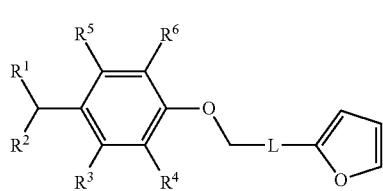

Structure I-D

In some examples of Formula I, if $R^1$ and $R^2$ are methyl, $R^3$, $R^4$, $R^5$, and $R^6$ are hydrogen, and Ar is unsubstituted furan, then L is not

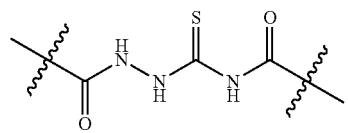

A particular example of Formula I is compound RNPA-2000:

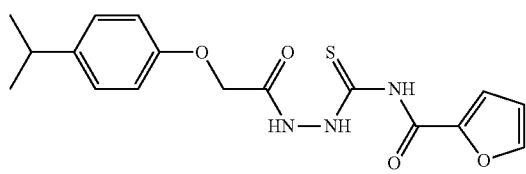

RNPA-2000

A second group of inhibitors includes compounds represented by Formula II:

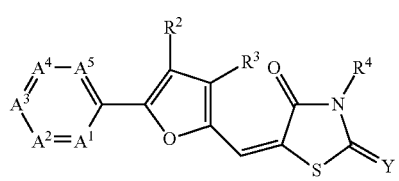

(II)

and pharmaceutically acceptable salts and prodrugs thereof.

In Formula II, $A^1$, $A^2$, $A^3$, $A^4$, and $A^5$ are each independently selected from N and $CR^1$. $R^1$ is selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl. In some examples, $A^1$, $A^2$, $A^3$, $A^4$, and $A^5$ are each $CR^1$. In some examples, $A^3$ is —CCl.

Also in Formula II, $R^2$ and $R^3$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl. In some examples, $R^2$ and $R^3$ are both hydrogen.

Additionally in Formula II, $R^4$ is selected from hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, or substituted or unsubstituted heteroalkyl. In some examples, $R^4$ contains a carboxylic acid. For example, $R^4$ can be —$CH_2CH_2CO_2H$. In some examples, $R^4$ can be substituted or unsubstituted aryl or substituted or unsubstituted heteroaryl. These examples can be represented by Structure II-A:

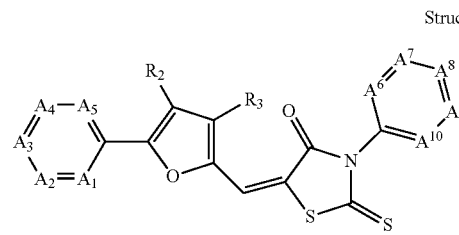

Structure II-A

In Structure II-A, $A^6$, $A^7$, $A^8$, $A^9$, and $A^{10}$ are each independently selected from N and $CR^6$. $R^6$ is selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl.

Further in Formula II, Y is O, S, or $NR^5$. $R^5$ is selected from hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, or substituted or unsubstituted heteroalkyl. In some examples, Y is S. These examples can be represented by Structure II-B:

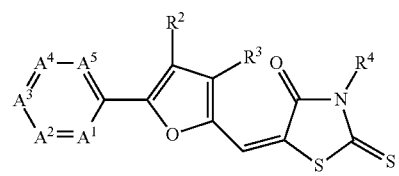

Structure II-B

Optionally, Y can be $NR^5$. These examples can be represented by Structure II-C:

Structure II-C

In Formula II, adjacent R groups, e.g., two adjacent $R^1$ groups or $R^2$ and $R^3$, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. For example, $R^2$ can be a substituted or unsubstituted ethylene group and $R^3$ can be a substituted or unsubstituted propylene group that combine to form a substituted or unsubstituted phenyl.

In some examples of Formula II, if $A^1$, $A^2$, $A^4$, and $A^5$ are CH, $R^2$ and $R^3$ are hydrogen, $A^3$ is CCl, and Y is S, then $R^4$ is not —$CH_2CH_2CO_2H$.

A particular example of Formula II is compound RNPA-3000:

RNPA-3000

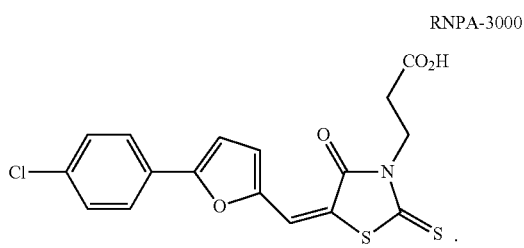 [SMILES: O=C(O)CCN1C(=O)/C(=C\c2ccc(-c3ccc(Cl)cc3)o2)SC1=S]

Pharmaceutical Compositions

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection can comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as can be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught herein.)

Administration of the compounds and compositions described herein or pharmaceutically acceptable salts thereof to a subject can be carried out using therapeutically effective amounts of the compounds and compositions described herein or pharmaceutically acceptable salts thereof as described herein for periods of time effective to treat a disorder.

The effective amount of the compounds and compositions described herein or pharmaceutically acceptable salts thereof as described herein can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. The expression effective amount, when used to describe an amount of compound in a method, refers to the amount of a compound that achieves the desired pharmacological effect or other effect, for example an amount that results in bacterial enzyme inhibition.

Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Methods of Making the Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on Formula I and Formula II include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Compounds of Formula I can be prepared from BOC-protected hexahydropyridazine or pyrazolidine starting materials (Zhang et al., 2003) using the parallel synthesis amenable methodology outlined in Scheme 1. Diversity can be introduced in the first or fourth steps of the sequence.

Scheme 1:

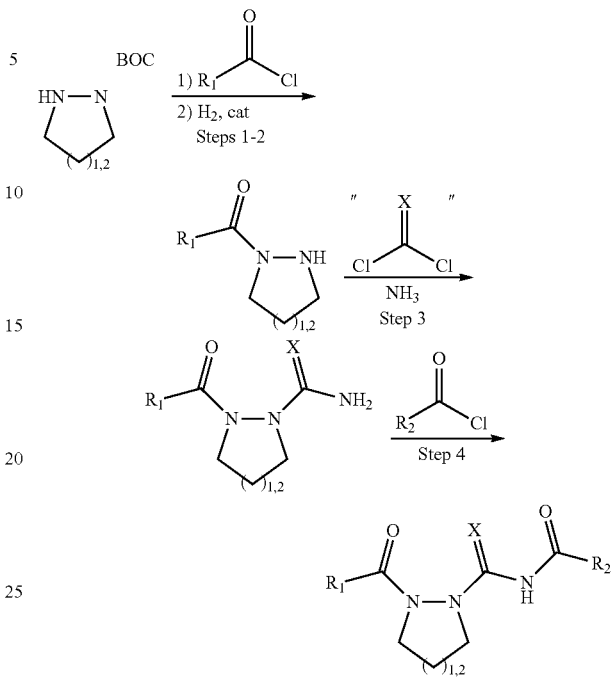

Hydroxyimide compounds of Formula I can be prepared using the methodology shown in Scheme 2. Knovenagal condensation will provide the required diester intermediates (Chikauchi et al., 2008), which can be converted to the required N-hydroxy-maleimides via the intermediate maleic anhydrides (Sankawa and Shibata, 1969). Additional diversity can be achieved through alternate synthetic methodology employing Suzuki chemistry (Selles, 2004).

Scheme 2:

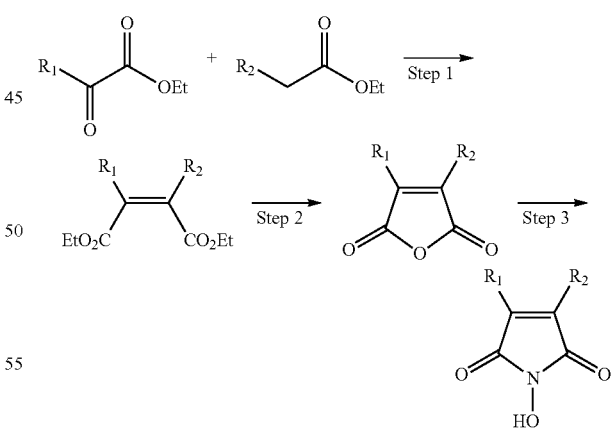

Further examples of Formula I can be prepared according to the method shown in Scheme 3. Treatment of acid chlorides with ammonium thiocyanate, followed by the appropriate hydrazide, gives the desired target molecules. Parallel synthesis technology can be used to rapidly expand the diversity of this scaffold by reversing the order of addition of the reagents (see Scheme 3). Subsequent treatment with potassium iodate provides analogous diacetyl hydrazides. Any structural modifications that enhance potency will be examined in combination with alternate chelating groups that show promise.

Scheme 3:

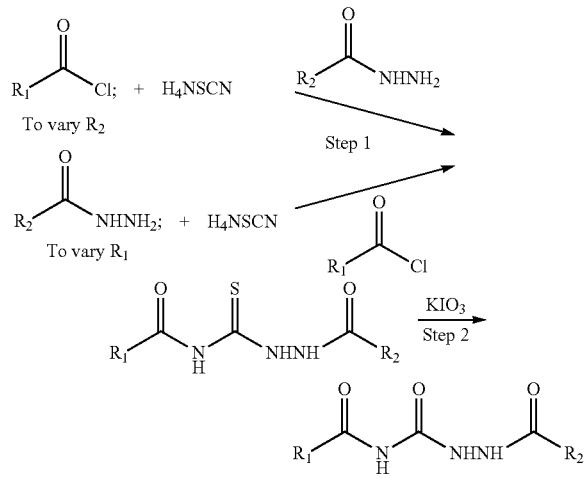

Compounds of Formula II can be prepared using general procedures available in the literature that are amenable to parallel synthesis (see Scheme 4). Furfuraldehydes can be purchased or prepared under Suzuki conditions using the commercially available reagent fur-furaldehyde-5-boronic acid. Condensation of the resulting intermediate with a protected rhodanine derivative followed by deprotection provides the penultimate intermediate, which can be treated with various electrophiles to give RNPA3000 analogs.

Scheme 4:

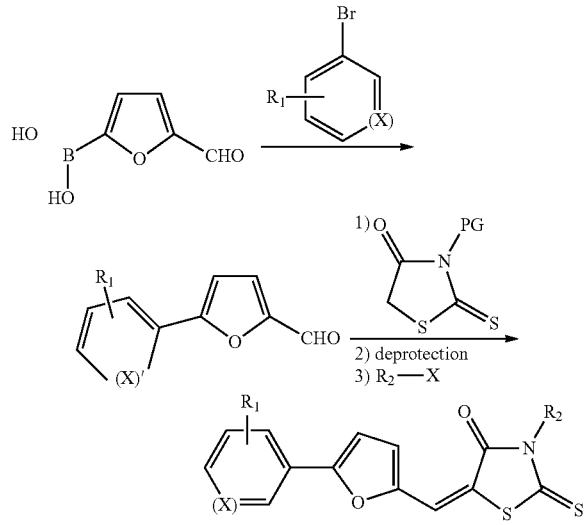

A similar strategy can be employed to generate compounds of Formula II possessing heterocyclic bioisosteres of the furan moiety as well as bioisosteres of the thioxothiazolidine ring (e.g., oxazolidinediones undergo similar condensations (Simchen and Seigl, 1992)). The general synthetic procedure of Cherbuliez et al. (1964) can be used to prepare these compounds (see Scheme 5). N-Arylrodanine intermediates can be prepared by condensing phenylthioisocyanates with mercapto-acetic acid. Treatment with the substituted furfuraldehydes, as depicted above in Scheme 4, yields the desired target molecules.

Scheme 5:

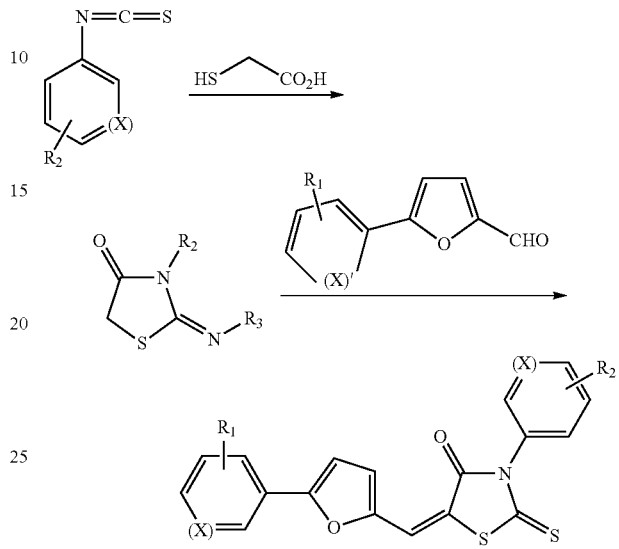

A similar sequence (Sahu et al., 1985) provides compounds of Formula II as shown in Scheme 6. Condensation of amines with isothiocyanates and chloroacetic acid provided the required penultimate intermediates, which can be converted to the desired final target compounds by treatment with the substituted furfuraldehydes.

Scheme 6:

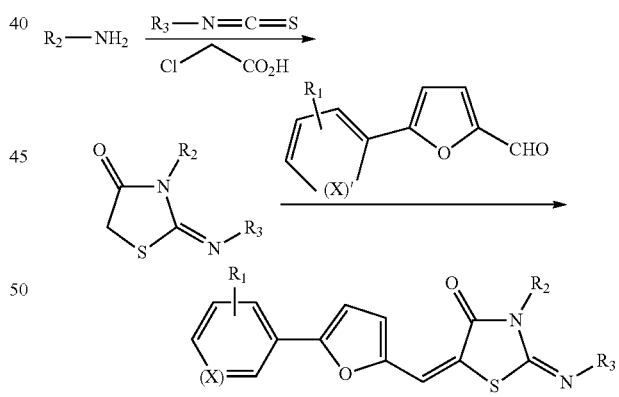

Activity Assays

Provided herein are methods of identifying a compound for treating or preventing a microbial infection. The methods can include preparing a compound or composition as described herein and assaying the inhibitory activity of the compound or composition against bacterial ribonucleases, such as RNase P. RNase P is an ubiquitous enzyme that catalyzes maturation of the 5' end of precursor tRNAs (see Frank et al., *Annu Rev Biochem*, 67: 153-180 (1998); Kazantsev et al., *Nat Rev Microbiol*, 4: 729-740 (2006); Walker et al., *Crit Rev Biochem Mol Biol*, 41: 77-102 (2006)). The enzyme is unique by virtue of the fact that it is a ribonucleoprotein complex, which includes a single ribozyme RNA molecule and at least one protein component. Within bacteria both the ribozyme (rnpB) and protein (RnpA) components are required for cell viability; rnpB mediates tRNA processing in vitro, whereas no function has been firmly established for RnpA (see Gossringer et al., *J Bacteriol*, 188: 6816-6823 (2006); Schedl et al., *Proc Natl Acad Sci USA*, 70: 2091-2095 (1973); Waugh et al., *J Bacteriol*, 172: 6316-6322 (1990)). Domain searches (see Letunic et al., *Nucleic Acids Res*, 34: D257-260 (2006); Schultz et al., *Proc Natl Acad Sci USA*, 95: 5857-5864 (1998)) revealed that *S. aureus* RnpA residues 40-111 best conform to a ribonuclease-like motif. Further, several RNA binding sites are embedded within this region (see Spitzfaden et al., *J Mol Biol*, 295: 105-115 (2000)). *E. coli* and *B. subtilis* RNase P have been found to digest certain double-stranded RNA templates, such as guide-RNAs and 4.5 s RNA (see Lundblad et al., *Proc Natl Acad Sci USA*, 105: 2354-2357 (2008)). Cleavage of those templates strictly requires RnpA (see Liu et al., *Cell*, 77: 1093-1100 (1994); Marvin et al., *J Cell Biochem*, 108: 1244-1251 (2009)). As provided herein, RNase P mediated RNA digestion may be dependent on rnpB, RnpA, or both. Thus, RnpA modulates *S. aureus* RNA degradation.

RNA degradation can be used to identify compounds suitable inhibiting bacterial ribonucleases, and thus, suitable for treating or preventing a microbial infection. In some embodiments, a fluorescence based assay can be used to identify the compounds. The method can include the steps of combining RNA, RnpA, and a fluorescent dye to form a mixture, contacting the mixture with the compound, and monitoring RnpA-mediated total bacterial RNA degradation in the cell using fluorescence. Decreased fluorescence, as compared to a control, indicates RNA degradation. As used herein, decreased fluorescence refers to a lowering of fluorescence, as compared to a control, of at least about 1%. For example, decreased fluorescence can be a decrease in fluorescence of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%, as compared to a control. A compound that decreases the RnpA-mediated total bacterial RNA degradation, as compared to a control, can be identified as the compound for treating or preventing the microbial infection. A suitable fluorescent dye for use in the methods described herein includes Quant-iT RiboGreen® (Invitrogen; Carlsbad, Calif.).

In some examples, compounds can be further assayed using the Mueller Hinton (MH) broth antibacterial assay as specified by the Clinical and Laboratory Standards Institute MIC broth microdilution protocol (see Methods for Dilution Antimicrobial Susceptibility Tests for Bacteria That Grow Aerobically; Approved Standard, *In The Clinical and Laboratory Standards Institute* (*CLSI, formerly NCCLS*), 7$^{th}$ ed., January 2006, 26 (2), M7-A7; see also Performance Standards for Antimicrobial Susceptibility Testing; Eighteenth Informational Supplement, In *The Clinical and Laboratory Standards Institute* (*CLSI, formerly NCCLS*), January 2008, 28 (1), M100-S18).

The activity of the compounds and compositions provided herein as inhibitors of bacterial RNase can be measured in standard assays, e.g., HPLC assays. The compounds can be tested as inhibitors of bacterial RNase in a bacterial RNase enzyme assay. Compounds that are identified as bacterial RNase inhibitors are useful in treating or preventing microbial infections. The activities of the compounds and compositions as determined using the assays can be reported in terms of $IC_{50}$. As used herein, $IC_{50}$ refers to an amount, concentration, or dosage of a particular test compound that achieves a 50% inhibition of a maximal response in an assay that measures such response.

In certain aspects, the disclosed compounds and compositions need not actually be synthesized, but instead can be used as targets for any molecular modeling technique to predict and characterize interactions with bacterial RNase. This is achieved through structural information and computer modeling. Computer modeling technology allows visualization of the three-dimensional atomic structure of a selected molecule and the rational design of new compounds that will interact with the enzyme. The three-dimensional construct of the enzyme typically depends on data from x-ray crystallographic analyses or NMR imaging of the selected molecule. This data is available for bacterial RNase. The molecular dynamics require force field data (e.g., Merck Molecular Force Field). The computer graphics systems enable prediction of how a new compound will link to the enzyme and allow experimental manipulation of the structures of the compound to perfect binding specificity. Prediction of what the interactions will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other. Upon identification of compounds that interact in a desired way with bacterial RNase in silico, actual compounds can be synthesized and assayed as disclosed herein.

Methods of Use

Provided herein are methods to treat, prevent, or limit microbial infections in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating microbial infections and cancer in humans, e.g., pediatric and geriatric populations, and in animals, e.g., veterinary applications. Microbial infections include, for example, bacterial and fungal infections. Bacterial infections include infections caused by bacilli, cocci, spirochaetes, and vibrio bacteria. In some examples, the microbial infection is a bacterial infection (e.g., a Gram positive bacterial infection). In some examples, the bacterial infection is *Staphylococcus* infection, such as a *Staphylococcus aureus*. The compounds and compositions described herein are useful in treating a variety of *Staphylococcus aureus* infections, including drug-resistant *Staphylococcus aureus* infections and biofilm-associated *Staphylococcus aureus* infections. In some embodiments, the *Staphylococcus aureus* infection is methicillin-resistant *S. aureus* (*S. aureus* MRSA). In other embodiments, the *Staphylococcus aureus* infection is vancomycin-resistant *S. aureus*. Optionally, the *Staphylococcus aureus* infection is multi-drug resistant. In some examples, the compounds and compositions described herein can be used to treat *Bacillus* infections (e.g., *Bacillus anthracis* and *Bacillus cereus*), *Streptococcus* infections (e.g., *Streptococcus pneumoniae* and *Streptococcus pyogenes*), and *Enterococcus* infections (e.g., *Enterococcus faecalis* and vancomycin-resistant *Enterococcus*).

The methods of treatment or prevention described herein can further include treatment with one or more additional agents (e.g., an antibacterial agent). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents. For example, the compounds or compositions or pharmaceutically acceptable salts thereof as described herein can be combined into a pharmaceutical composition with an additional antibacterial agent, such as acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; Lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin; oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillin G benzathine; penicillin G potassium; penicillin G procaine; penicillin G sodium; penicillin V; penicillin V benzathine; penicillin V hydrabamine; penicillin V potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin B sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; or zorbamycin.

Further provided herein are methods of inhibiting a bacterial ribonuclease, such as the protein component of *Staphylococcus aureus* RNase P. In some embodiments, the bacterial ribonuclease is RnpA. The methods comprise contacting the bacterial ribonuclease with an effective amount of one or more of the compounds or compositions described herein. Such amounts are sufficient to achieve a therapeutically effective concentration of the compound or active component of the composition in vivo or in vitro.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of a bacterial infection), during early onset (e.g., upon initial signs and symptoms of a bacterial infection), or after an established inflammatory response or development of a bacterial infection. Prophylactic administration can occur for several days to years prior to the manifestation of symptoms of an infection. Prophylactic administration can be used, for example, in the preventative treatment of subjects exposed to *Staphylococcus aureus*. Therapeutic treatment involves administering to a subject a therapeutically effective amount of the compounds and compositions or pharmaceutically acceptable salts thereof as described herein after a bacterial infection is diagnosed.

Kits

Also provided herein are kits for treating or preventing inflammation or cancer in a subject. A kit can include any of the compounds or compositions described herein. For example, a kit can include a compound of Formula I or a compound of Formula II. A kit can further include one or more antibacterial agents (e.g., oxacillin). A kit can include an oral formulation of any of the compounds or compositions described herein. A kit can additionally include directions for use of the kit (e.g., instructions for treating a subject).

The examples below are intended to further illustrate certain aspects of the methods and compounds described herein, and are not intended to limit the scope of the claims.

EXAMPLES

*S. aureus* RNA degradation factors were empirically identified and, as demonstrated below, were proven to represent promising antimicrobial drug development targets. To do so, the fact that *S. aureus* owes its ability to cause infection, in part, to the temporal expression of an expansive repertoire of virulence factors, many of which are regulated in a cell density-dependent manner during laboratory culture conditions, was exploited (see Novick, R. P., *Mol Microbiol*, 48: 1429-1449 (2003)). Studies were then performed to determine whether growth phase regulated changes in *S. aureus* virulence factor expression occur at the level of mRNA degradation and whether the proteins involved in this process may include members of the organism's RNA degradation machinery. Accordingly, Affymetrix GeneChips were used to compare the mRNA decay rates of well-characterized *S. aureus* virulence factors during exponential- and stationary-phase growth.

Results revealed that the mRNA turnover properties of many *S. aureus* virulence factor transcripts differed between the two growth phases. Furthermore, the global mRNA decay properties of exponential and stationary phase cells were found to be dramatically different; 884 *S. aureus* mRNA species were stabilized during stationary phase growth. Among the genes whose expression correlated with mRNA decay was the protein component of ribonuclease P, RnpA, suggesting that it may play a role in bulk mRNA turnover. Consistent with that possibility, it was demonstrated that recombinant *S. aureus* RnpA exhibits ribonuclease activity in vitro and RnpA depleted cells exhibit reduced mRNA degradation. Because RnpA is an essential *S. aureus* enzyme with low amino acid conservation with mammalian proteins, it is an appropriate target for antimicrobial drug discovery. Accordingly, high through-put and secondary screening assays were used to identify small molecule inhibitors of RnpA-mediated RNA degradation. One of these agents was shown to inhibit *S. aureus* mRNA turnover, exhibited antimicrobial activity against MRSA, VISA, and VRSA, as well as other Gram-positive pathogens with high RnpA conservation, and limited pathogenesis in a murine acute lethal model of infection. Collectively these results demonstrate that RnpA is a previously uncharacterized member of the *S. aureus* RNA degradation machinery and validate its utility as an antimicrobial drug discovery target.

Example 1

Growth-Phase Dependent Alternations in *S. aureus* Turnover

For half life determinations, *S. aureus* strain UAMS-1, RN4220 (pCN51; plasmid containing $CdCl_2$ inducible promoter), RN4220 (pRNPA; pCN51 capable of producing full length rnpA mRNA), or RN4220 (pRNPA-A.S.; pCN51 capable of producing rnpA antisense RNA) were grown to mid-exponential or stationary phase, transcription was arrested by the addition of rifampin (200 µg/ml), and aliquots were removed at 0-, 2.5-, 5-, 15- and 30-min post-transcriptional arrest for strain UAMS-1. To conserve reagents, aliquots were removed at 0 and 10 min post-transcriptional arrest for RN4220 derivatives. Plating ensured cultures had not developed rifampin resistance. Each strain and/or growth phase was assessed twice, except for RN4220 pRNPA-A.S. cells which were assessed four times. RNA was isolated from each aliquot, labeled, hybridized to an *S. aureus* GeneChip (Affymetrix; Santa Clara, Calif.), duplicates were averaged, and the mRNA half-lives of all mRNA species were determined, as previously described (see Anderson et al., *J Bacteriol*, 188: 6739-6756 (2006); Roberts et al., *J Bacteriol*, 188: 2593-2603 (2006)). To measure the mRNA turnover characteristics of inhibitor-challenged cells, exponential-phase *S. aureus* were treated with 0.5×MIC of the RnpA inhibitor or equivalent volume compound solvent (DMSO) for 30 min. Transcript synthesis was then arrested and the transcript titers of mRNA species were measured at 0- and 5-min post-transcriptional arrest (see Anderson et al., *J Bacteriol*, 188: 6739-6756 (2006); Roberts et al., *J Bacteriol*, 188: 2593-2603 (2006)).

The results demonstrated that the mRNA turnover properties of many (41%) virulence factor transcripts differed between the two growth phases, suggesting that regulated changes in mRNA turnover may affect their expression. Moreover, it was observed that the organism produced at least five stationary phase specific small stable RNAs (SSRs), a hypothesized class of regulatory non-coding RNA molecules (see Anderson et al., *J Bacteriol*, 188: 6739-6756 (2006); Roberts et al., *J Bacteriol*, 188: 2593-2603 (2006)). Further, the global mRNA turnover properties of exponential- and stationary-phase cells differed considerably. Consistent with previous measurements, it was found that most (90%) exponential phase transcripts are rapidly degraded (half life of ≤5 min), 9% exhibit intermediate stability (half life of >5 min but ≤30 min), and 1% are stable (half life of ≥30 min) (see Anderson et al., *J Bacteriol*, 188: 6739-6756 (2006); Roberts et al., J Bacteriol, 188: 2593-2603 (2006)). However, during stationary phase growth, 76%, 21%, and 3% of mRNA species exhibit short, intermediate, and stable half lives, respectively (FIG. 1). Neither RNase J1 nor RNase Y were found to be differentially expressed in a growth phase dependent manner. Among the 367 genes repressed during stationary phase growth was rnpA, which codes for the protein component of ribonuclease P (RNase P).

Example 2

S. aureus RnpA Exhibits Ribonuclease Activity and Affects Cellular mRNA Degration Protein Purification Each putative *S. aureus* ribonuclease predicted open reading frame was PCR amplified and inserted into the ligation-independent cloning site of plasmid pET-30 Ek/LIC (Novagen; Madison Wis.). Sequencing confirmed that this fused a hexahistidine-tag to the N-terminus of each protein under the control of the plasmid's isopropyl β-D-1-thiogalactopyranoside (IPTG) inducible promoter. Following transformation, each protein was purified from *E. coli* BL21 (DE3) cells grown in the presence of IPTG (4 hr) by $Ni^{+2}$ affinity chromatography. More specifically, 10 g of cell pellet was suspended in 50 ml of buffer A (300 mM NaCl, 50 mM $Na_2HPO_4$, pH 7.4) containing a complete mini EDTA-free protease inhibitor tablet (Roche; Branford, Conn.) and 20 mM imidazole. Cells were ruptured by seven passes at 15,000 psi through an Emulsifex-C3 microfluidizer (Avestin Inc.; Ottawa, Canada). Cell debris was removed by centrifugation at 12,000×g for 30 min and supernatants were loaded onto a 5 mL Ni-NTA FF-crude affinity column (GE Healthcare Bio-Sciences; Piscataway, N.J.) with an AKTA-FPLC high performance liquid chromatography system (GE Healthcare Bio-Sciences; Pittsburgh, Pa.). Proteins eluted in a single peak with a linear imidazole gradient (80 mM to 500 mM) in buffer A. The presence of each protein was assessed by Coomasie stained SDS-PAGE and matrix-assisted laser desportion/ionization (MALDI) analysis spectrometry (Wistar Institute; Philadelphia, Pa.).

Plasmids

Plasmids pRNPA-S and pRNPA-A.S. contain the putative rnpA transcriptional unit including predicted Shine-Delgarno sequence in the sense and antisense orientation, respectively under control of the $CdCl_2$ inducible of the *S. aureus* shuttle-vector pCN51 (see Charpentier et al., *Appl Environ Microbiol*, 70: 6076-6085 (2004)). Briefly, the rnpA open reading frame and 34 nt upstream sequence was PCR amplified from *S. aureus* strain UAMS-1 using primers 5' GAATTCTCAAATAAAAACGATAAATAAGCGAGTG-ATGTTA (forward) SEQ ID. No. 1) and 5' GGTACCTTACTTAATCTTTTTATTAAAAACTTTGG-CAA (reverse) (SEQ ID No. 2) containing a 5' terminal EcoRI and KpnI restriction enzyme site (underlined), respectively, or primers in which the restriction enzyme sequence had been reversed. Resulting PCR products were ligated into pCRII-TOPO vector and transformed into *E. coli* INVαF' cells for propagation (Invitrogen, Carlsbad, Calif.). Plasmid DNA was subsequently purified using QIAprep Spin Miniprep Kits (Qiagen, Valencia, Calif.) then digested with EcoRI and KpnI to liberate the plasmid inserts, which were gel purified using a QIAquick Gel Extraction Kit (Qiagen) and ligated into EcoRI and KpnI-digested pCN51. DNA sequencing confirmed the integrity of plasmid pRNPA-S and pRNPA-A.S.

Western Blotting

Affinity purified PolyQuik rabbit *S. aureus* RnpA polyclonal antibodies were generated by Invitrogen (Carlsbad, Calif.). Total bacterial proteins were isolated from RN4220 cells containing plasmid vector (pCN51), RnpA overexpressor plasmid (pRNPA-S) or RnpA antisense RNA plasmid (pRNPA-A.S.) following 30 min growth in TSB medium supplemented with 2.5 μM $CdCl_2$ to induce RNA expression and 10 μg/ml erythromycin for plasmid maintenance. Resultant protein concentrations were determined by conventional Bradford Assays and 2.0 μg of each protein sample or purified *S. aureus* RnpA was electrophoresed in a 10% SDS polyacrylamide gel and transferred to a polyvinylidene fluoride membrane (Millipore, Billerica, Mass.). Membranes were blocked with 10% milk, washed, incubated with rabbit RnpA antibody (1:1000 dilution), washed, incubated with horseradish peroxidase-conjugated anti-rabbit antibody (1:1000 dilution; GE Healthcare) and processed using an Amersham ECL Western Blotting System, according to the manufacturer's recommendations (GE Healthcare).

Results

Figure 2A:
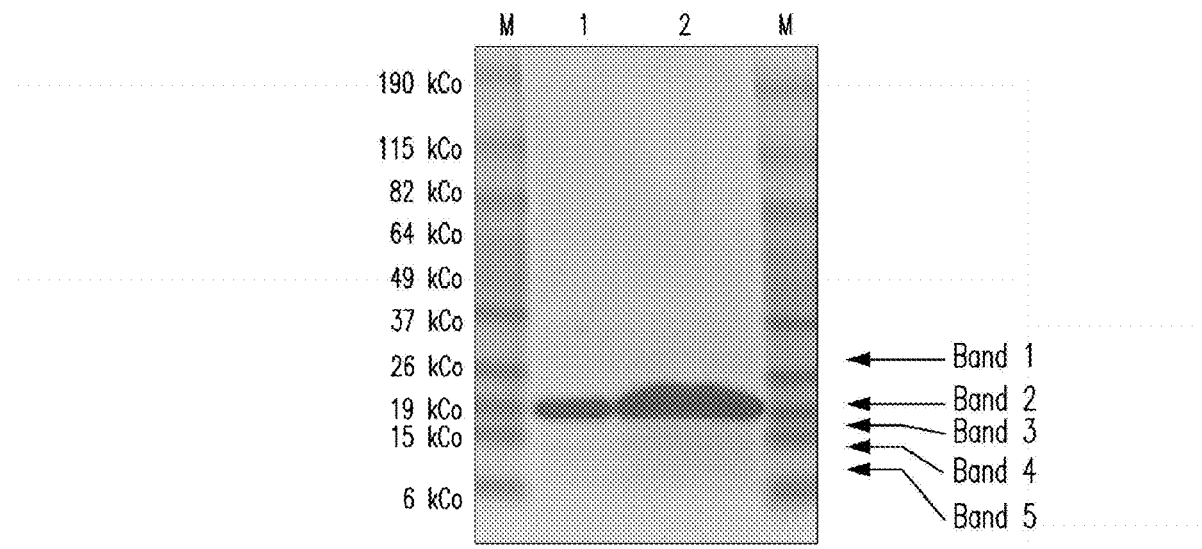
FIGS. 2A, 2B, 2C, 2D, and 2E demonstrate that *S. aureus* RnpA catalyzes rRNA and mRNA digestion.
Figure 2B:
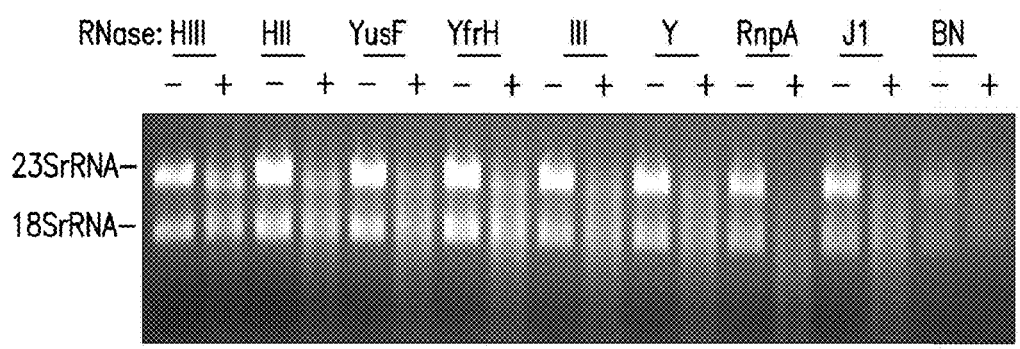
Figure 2C:
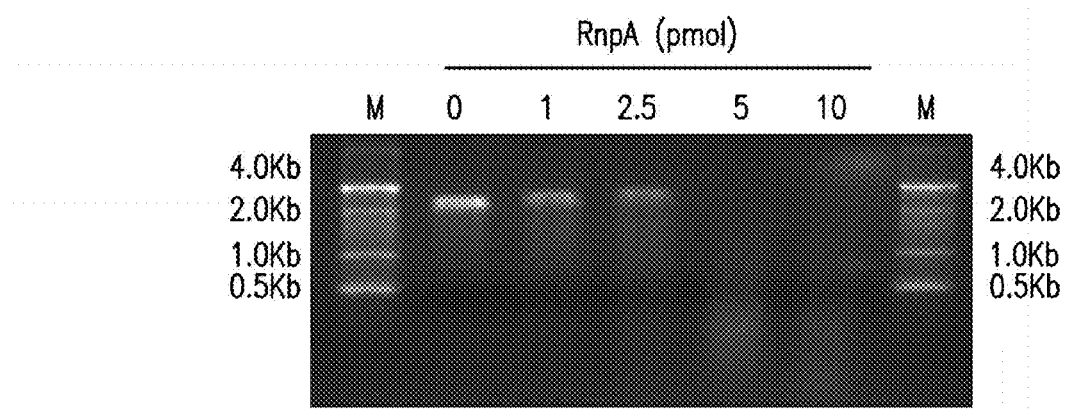

Recombinant *S. aureus* RnpA was found to catalyze digestion of rRNA and staphylococcal protein A (spa) mRNA (FIGS. 2B and 2C), as well as three other mRNA species tested. Other putative *S. aureus* ribonucleases including RNase III, RNase HII, RNase HIII, RNase Y, RNase J1, and BN did not exhibit equivalent RNA degradation activity during these assay conditions (FIG. 2B). SDS-PAGE and matrix-assisted laser desorption/ionization (MALDI) analysis confirmed that the observed ribonuclease activity was associated with the presence of *S. aureus* RnpA (FIG. 2A). In FIG. 2A, the band at ~17.2 kDa (solid arrow; Band 2) was confirmed to be *S. aureus* RnpA by tandem mass spectrometry (Wistar Institute; Philadelphia, Pa.), whereas top-hits for minor contaminants (dashed arrows) were determined to be *E. coli* 505 ribosomal protein L3 (Band 1) or *S. aureus* RnpA polypeptide fragments, corresponding to amino acids 11-107 (Bands 3 and 4) or 12-107 (Band 5). Nonetheless, SDS-PAGE assessment of approximately 1000-fold excess (25 μg) of RnpA purification product used in the aforementioned ribonuclease assays revealed trace amounts of four additional polypeptides within the protein preparation, raising the possibility that contaminating *E. coli* ribonucleases may be present with the RnpA product. MALDI analysis revealed the identity of these proteins to be *E. coli* ribosomal protein L3, and three *S. aureus* RnpA fragments, presumably reflecting proteolytic degradation of full length RnpA during protein preparation as opposed to mature alternative translation products. No *E. coli* ribonucleases were detected, suggesting that the protein preparation's ribonucleolytic activity could be attributed to *S. aureus* RnpA. Moreover, reverse transcriptase mediated PCR revealed that *E. coli* rnpB was undetectable within the preparation, establishing that RnpA ribonuclease activity was not due to the formation of chimeric RNase P molecules consisting of *S. aureus* RnpA and *E. coli* rnpB RNA. Indeed, in vitro synthesized *E. coli* rnpB neither catalyzed *S. aureus* RNA degradation (alone) nor affected the activity of RnpA-mediated RNA digestion during both standard and elevated $Mg^{+2}$ reaction conditions.

While *S. aureus* RNase J1 exhibited low ribonucleolytic activity in the reaction conditions used here, subsequent studies revealed that it is a potent ribonuclease in differing buffering conditions (see Even et al., *Nucleic Acids Res*, 33: 2141-2152 (2005)) and could be used as a control to further evaluate the putative in vitro ribonuclease activity of *S.*

Figure 2D:
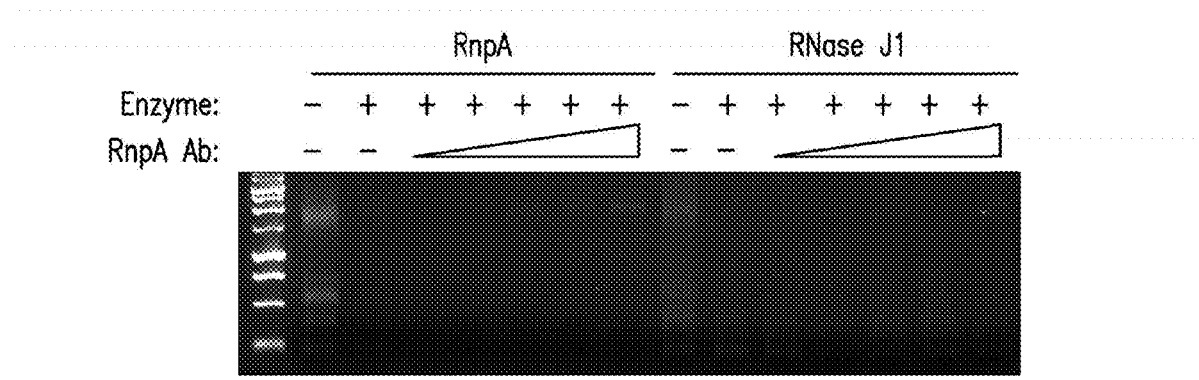
Figure 2E:
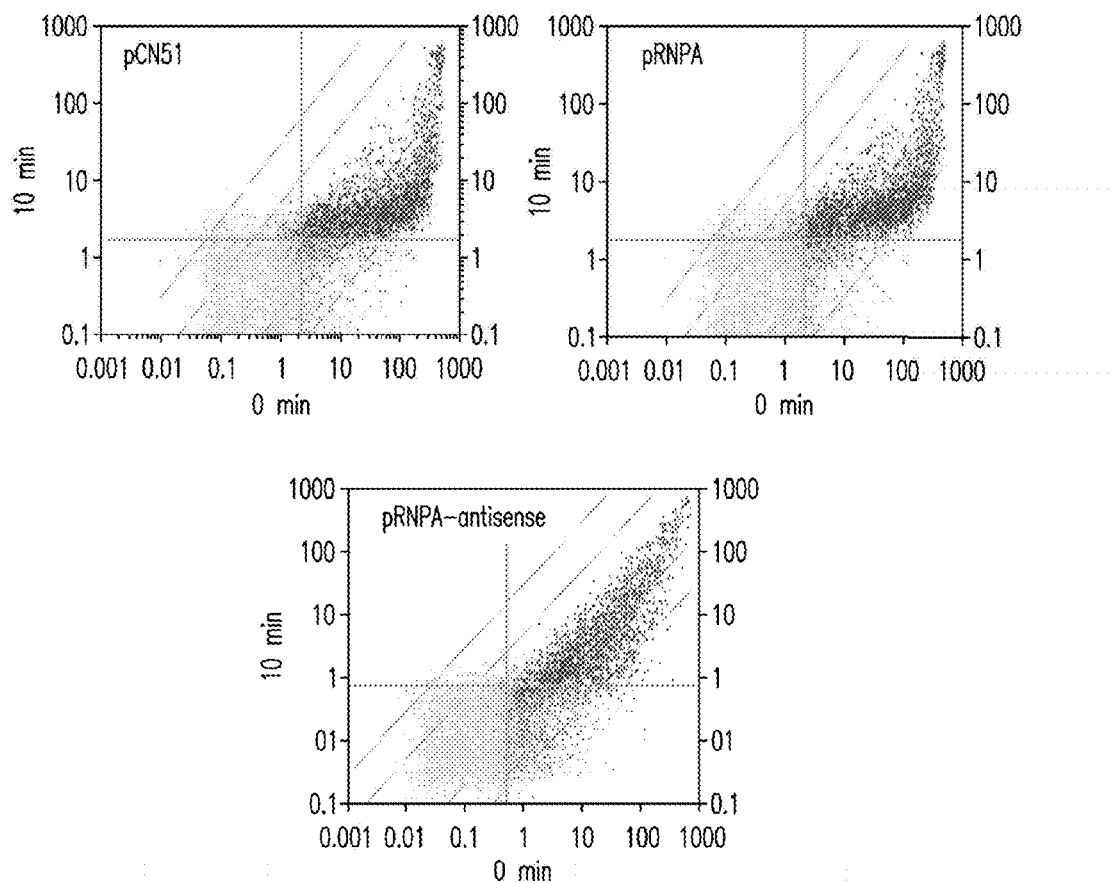

*aureus* RnpA. More specifically, it was assessed whether RnpA-mediated spa mRNA degradation could be inhibited by the addition of affinity purified rabbit polyclonal *S. aureus* RnpA antibodies. Initial studies did not reveal that antibody limited either RnpA or RNase J1 ribonucleolytic activity. However, anticipating that the only a subset of antibodies within the immunoglobulin mixture may recognize RnpA epitope(s) that affect the enzyme's activity, reverse transcription PCR amplification of spa-digested products was used as a more sensitive means of monitoring what, if any, effect the antibody had on RnpA-mediated transcript degradation. Results revealed that antibody addition did indeed weakly inhibit RnpA-mediated degradation of full length spa mRNA but had no effect on RNase J1 activity (FIG. 2D). Equivalent amounts of pre-immune serum had no effect on RnpA activity. Taken together, these data suggest that a previously unrecognized function *S. aureus* RnpA is that of RNA digestion.

Figure 3A:
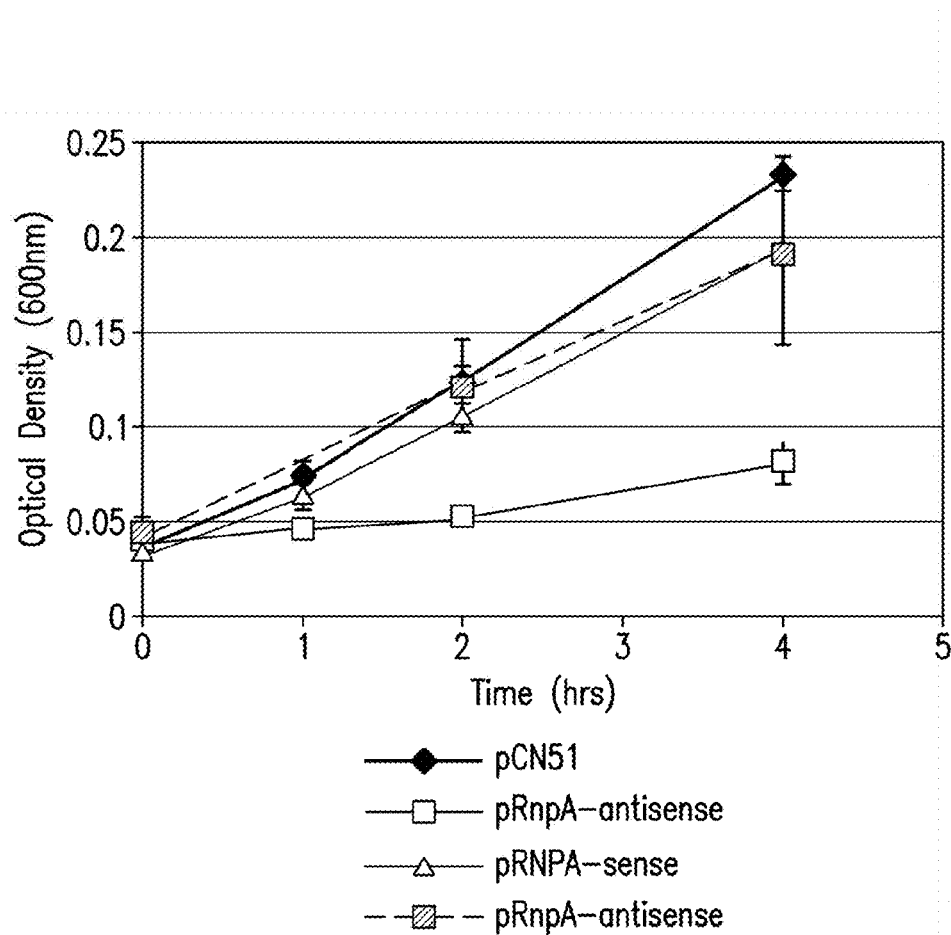
FIG. 3A depicts plots of the growth characteristics (optical density; Y-axis), for *S. aureus* strain RN4220 containing vector (pCN51; diamonds), rnpA sense RNA (pRNPA-S; triangles) and rnpA antisense RNA (pRNPA-A.S.; squares) when grown in the presence of 10 μM $CdCl_2$.
Figure 3B:
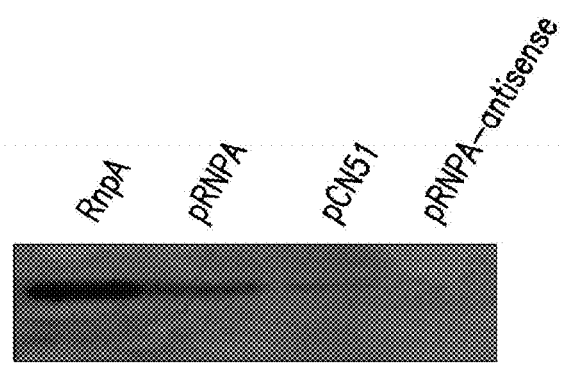
FIG. 3B shows the Western blotting results for *S. aureus* strain RN4220 pCN51 (vector), RN4220 pRNPA (overexpressor), and RN4220 pRNPA-A.S. (RnpA depleted) cells grown in the presence of 2.5 μM $CdCl_2$.
Figure 4A:
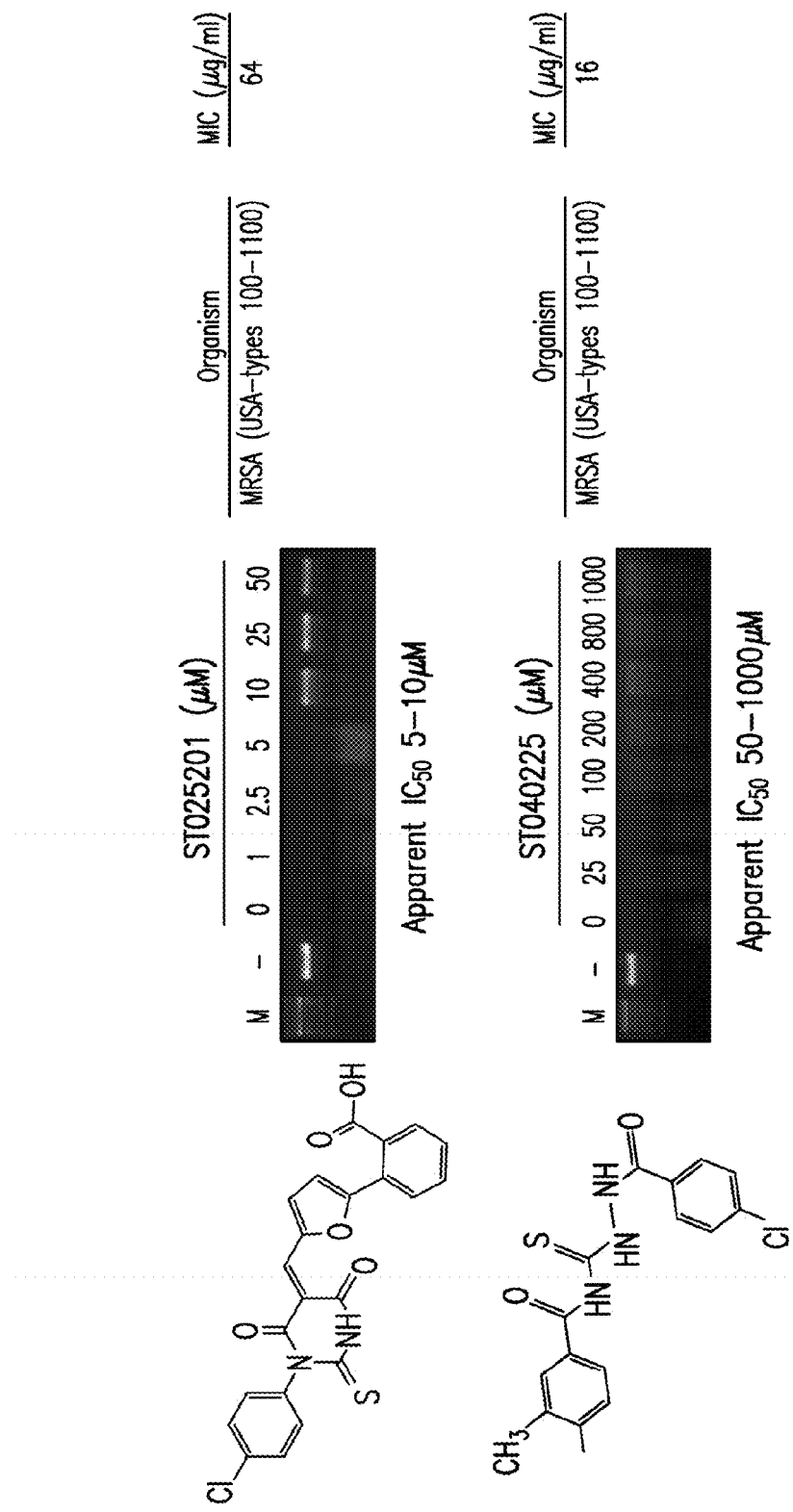
FIGS. 4A and 4B show structures of compounds tested for RnpA inhibition, the apparent IC50 measurements, and the median minimal inhibitory concentration (MIC) for all U.S. methicillin resistant *S. aureus* lineages and other organisms.
Figure 4B:
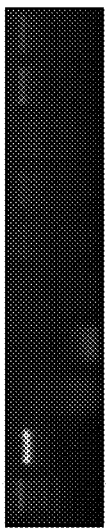
Figure 4B:
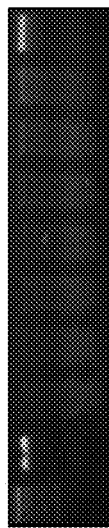
Figure 4B:
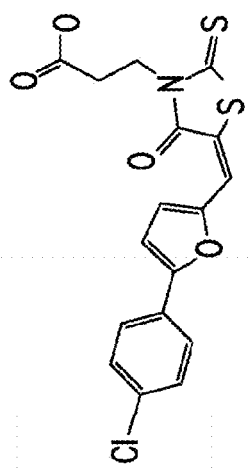
Figure 4B:
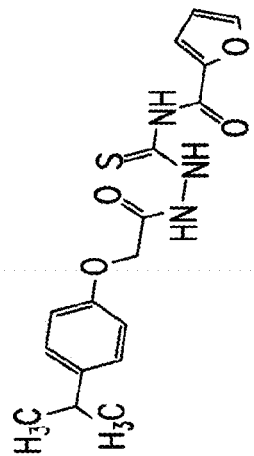

Small molecule inhibitors of essential bacterial RNA turnover proteins are expected to interfere with bacterial growth and represent a new class of antimicrobial agents. In that regard, *S. aureus* RnpA is a reported essential enzyme (see Chaudhuri et al., *BMC Genomics*, 10: 291 (2009); Ji et al., *Science*, 293: 2266-2269 (2001)) and thus could be considered a target for chemotherapeutic development. Indeed, induction of an antisense RNA molecule that is predicted to be complementary to the −34 to +353 rnpA mRNA translation start site (under control of the cadmium chloride inducible promoter of plasmid, pCN51 (see Charpentier et al., *Appl Environ Microbiol*, 70: 6076-6085 (2004)) limited *S. aureus* proliferation in the presence of 10 µM inducer. Conversely, no growth defects were observed for cells expressing the corresponding sense strand RNA molecule or the antisense plasmid strain in the absence of inducer (FIG. 3). These results indicate that *S. aureus* RnpA is an essential protein. Further, using this rnpA antisense RNA system, it was assessed whether RnpA affects *S. aureus* cellular mRNA turnover. Accordingly, the RNA degradation properties were measured for cells harboring plasmid vector alone or cells containing plasmid borne copies of rnpA mRNA or rnpA antisense RNA during growth in the presence of 2.5 µM $CdCl_2$. As shown in FIG. 3, 2.5 µM cadmium chloride was empirically determined to be the optimal concentration that allowed increased- or decreased-RnpA production within rnpA mRNA or rnpA antisense expressing strains, respectively, but did not limit bacterial growth of the antisense RNA producing strain. Accordingly, RNA turnover analyses revealed that diminished RnpA levels correlated with the stabilization of many mRNA species, suggesting that the enzyme contributes to bulk cellular RNA degradation. More specifically, it was found that 88% and 87% of all exponential phase transcripts produced in RnpA overexpressing and vector containing cells exhibited a half life of less than 10 min, respectively. The finding that RnpA overexpression did not accelerate cellular RNA degradation may indicate that the protein's RNA degradation activity is dependent on co-factors, which remain at wild type levels or that the protein did not reach a concentration that effectively increases RNA turnover.

Example 3

Identification of Small Molecule Inhibitors of RnpA-Mediated RNA Degradation

The above results indicate that *S. aureus* RnpA is an essential enzyme that exhibits in vitro ribonuclease activity and participates in cellular RNA degradation. Moreover, the protein is well conserved across Gram-positive bacteria but lacks amino acid conservation with mammalian proteins, making it an attractive target for novel antibiotic drug development. Accordingly, a fluorescence-based high through-put assay was used to screen 29,066 commercial compounds (ActiProbe-25K and Natural product libraries; Timtec; Newark, Del.) for small molecule inhibitors of RnpA-mediated RNA degradation.

Specifically, members of the ActiProbe-25K and Natural Product libraries (29,940 compounds total; TimTec Inc.; Newark, Del.) were screened for small molecule inhibitors of *S. aureus* RnpA mediated total bacterial RNA degradation. All reactions (50 µl) were performed in 96-well format and contained 20 pmol RnpA, 200 ng *S. aureus* total RNA, and ~5 µM of each compound in 1× reaction buffer (2 mM NaCl, 2 mM $MgCl_2$, 50 mM Tris-HCl, pH 6.0). Mixtures were incubated at 37° C. for 20 min at which time Quant-iT RiboGreen® (100 µl; Invitrogen) was added to quantify the amount of RNA substrate remaining. Percent enzyme inhibition was calculated as remaining substrate/starting substrate*100. For inhibitory titration assays, 1 pmol of spa mRNA was incubated with 20 pmol RnpA alone (positive control) or in the presence of one of four compounds for one hour at 37° C. The compounds included RNPA-2000 (labeled in FIG. 4 as ST003531) in increasing amounts (0, 2.5, 5, 10, 12.5, 15, 17.5, and 20 µM); RNPA-3000 (labeled in FIG. 4 as ST0006630) in increasing amounts (0, 2.5, 5, 10, 12.5, 15, 20, and 25 µM); ST040225 in increasing amounts (0, 25, 50, 100, 200, 400, 800, and 1000 µM); and ST025201 (0, 1, 2.5, 5, 10, 25, and 50 µM). Following this, 20 µl of each reaction mixture were subjected to electrophoresis in a 1.2% formaldehyde-containing agarose gel and visualized by ethidium bromide staining.

Compounds RNPA-2000, RNPA-3000, and ST025201 were shown to inhibit RnpA-mediated RNA degradation against the 10 predominant U.S. MRSA lineages (see FIG. 4). The apparent $IC_{50}$ values for RNPA-2000, RNPA-3000, and ST025201 were 15-20 µM, 12.5-20 µM, and 5-10 µM respectively.

Example 4

Antimicrobial Susceptibility Testing

In vitro activities of RNPA-2000 (labeled in FIG. 4 as ST003531), RNPA-3000 (labeled in FIG. 4 as ST0006630), ST040225, and ST025201 against bacteria were determined by the broth microdilution method according to the Clinical and Laboratory Standards Institute (CLSI) guidelines using cation adjusted Mueller-Hinton broth or MH broth supplemented with 5% lysed horse blood (for testing *Streptococcus* spp.). Microtiter plates containing serial dilutions of the compounds 1000 (0, 4, 8, 16, 32, 64, and 128 µg/ml) were inoculated with $10^5$ colony forming units (CFU)/ml and incubated for 18 hr at 37° C. The MIC for each isolate was defined as the lowest concentration of each of the compounds that completely inhibited growth of the organism as detected by the unaided eye. As shown in FIG. 4, RNPA-2000, RNPA-3000, and ST040225 demonstrated moderate antimicrobial activity against the MRSA.

Example 5

Cytotoxicity Assays

It was then assessed whether RnpA-inhibitory agent concentrations corresponding to the effective bacterial MIC values (10-50 µg/ml) elicited human cell cytotoxicity. HepG2 human hepatocytes ($10^5$ cells) were seeded in individual wells of a microtitre plate and incubated for 16 hr at 37° C. with 5% carbon dioxide in Dulbecco's Modified Eagle Media supplemented with 10% fetal bovine serum. Cells were then challenged with Mitomycin C (5 or 10 μg/ml; positive control) or 1, 2, or 4 times (1×, 2×, 4×) the MIC value of the indicated RnpA inhibitory compound for 48 hours. Cell viability was measured spectrophotometrically (570 nm) following the addition and subsequent reduction of tetrazolium salt (MTT) within metabolically active cells, as per the manufacturer's recommendations (American Type Culture Collection; Manassas, Va.).

Figure 5:
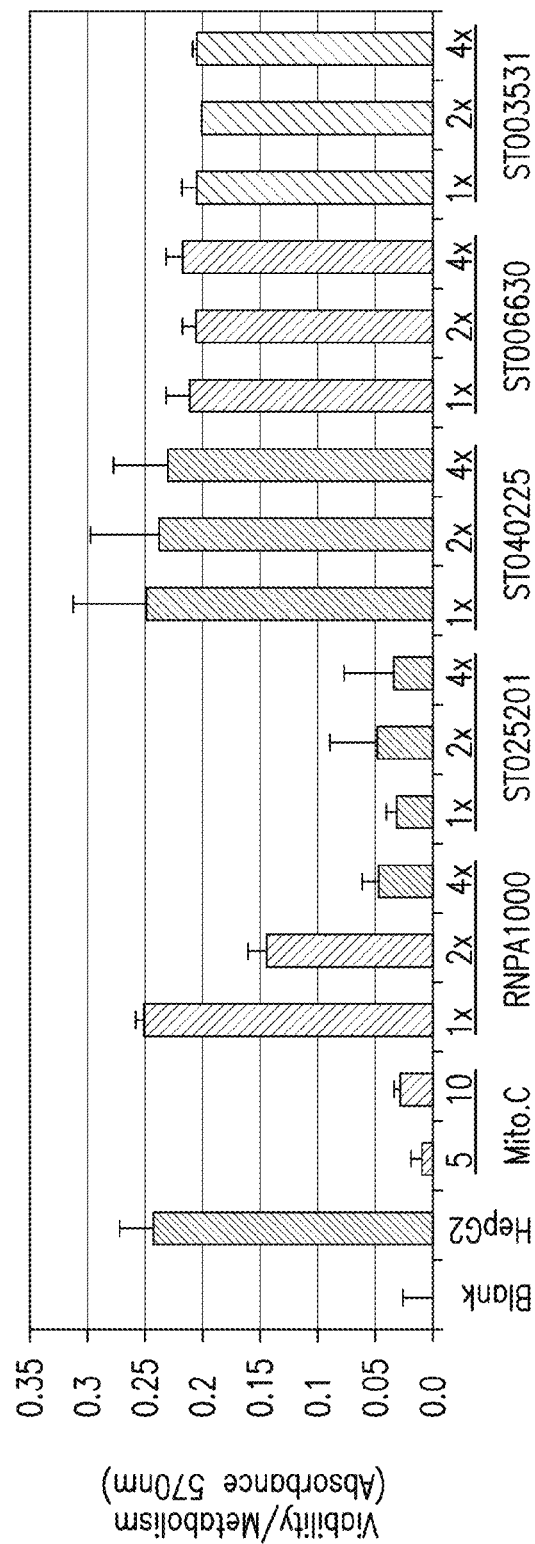
FIG. 5 shows the cytotoxicity assay results from HepG2 cells challenged with 1, 2, or 4 times the MIC value of the indicated compound. HepG2 cells treated with DMSA served as a negative control (HepG2) and Mitomycin C treated (5 or 10 μg/ml) cells served as a positive control.

MTT cell proliferation assay measurements revealed that ST025201 elicits human toxic effects (see FIG. 5). Thus, while the agent inhibits RnpA and exhibits antimicrobial effects, it is not an appropriate lead molecule for further development. Conversely, ST040225, ST006630 (i.e., RNPA-3000), and ST003531 (i.e., RNPA-2000) did not affect human cell survival (see FIG. 5). In summary, RNPA-2000 and RNPA-3000 exhibit excellent RnpA-inhibitory activity, good antistaphylococcal activity, and do not cause human cytotoxicity.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A method of treating, reducing, or inhibiting a bacterial infection in a subject, comprising administering to the subject an effective amount of an RNase inhibitor of the following structure:

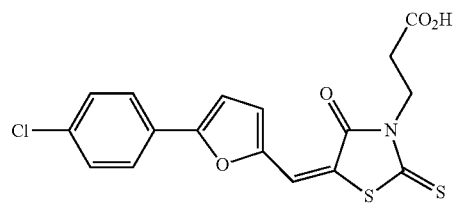 [SMILES: O=C(O)CCN1C(=O)/C(=C\c2ccc(-c3ccc(Cl)cc3)o2)SC1=S]

or a pharmaceutically acceptable salt or prodrug thereof,
wherein the bacterial infection is a *Staphylococcus* infection.

2. The method of claim 1, wherein the *Staphylococcus* infection is a *Staphylococcus aureus* infection.

3. The method of claim 2, wherein the *Staphylococcus aureus* infection is a drug-resistant *Staphylococcus aureus* infection.

4. The method of claim 2, wherein the *Staphylococcus aureus* infection is a biofilm-associated *Staphylococcus aureus* infection.

5. The method of claim 1, wherein the RNase inhibitor is a RnpA inhibitor.

6. The method of claim 1, further comprising administering a second compound, wherein the second compound is an antibacterial compound.

7. A method of inhibiting a bacterial ribonuclease comprising contacting the bacterial ribonuclease with an effective amount of an RNase inhibitor of the following structure:

SEQUENCE LISTING

<160> NUMBER OF SEQ ID NOS: 2

<210> SEQ ID NO 1
<211> LENGTH: 40
<212> TYPE: DNA
<213> ORGANISM: Artificial sequence
<220> FEATURE:
<223> OTHER INFORMATION: Synthetic construct

<400> SEQUENCE: 1
gaattctcaa ataaaaacga taaataagcg agtgatgtta                                40

<210> SEQ ID NO 2
<211> LENGTH: 38
<212> TYPE: DNA
<213> ORGANISM: Artificial sequence
<220> FEATURE:
<223> OTHER INFORMATION: Synthetic Construct

<400> SEQUENCE: 2
ggtaccttac ttaatctttt tattaaaaac tttggcaa                                  38

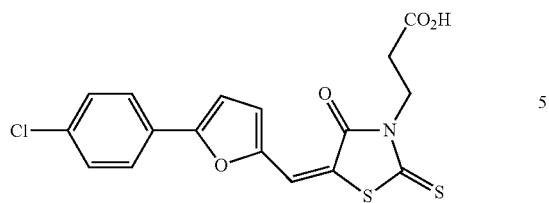
or a pharmaceutically acceptable salt or prodrug thereof, wherein the bacterial ribonuclease is *Staphylococcus aureus* RNase P.
8. The method of claim 7, wherein the bacterial ribonuclease is RnpA.
9. The method of claim 7, wherein the contacting occurs in vivo.
10. The method of claim 7, wherein the contacting occurs in vitro.
* * * * *

UNITED STATES PATENT AND TRADEMARK OFFICE
CERTIFICATE OF CORRECTION

PATENT NO. : 9,517,230 B2
APPLICATION NO. : 14/744205
DATED : December 13, 2016
INVENTOR(S) : Paul M. Dunman, Patrick D. Olson and Wayne Childers Page 1 of 1

It is certified that error appears in the above-identified patent and that said Letters Patent is hereby corrected as shown below:

In the Specification

In Column 1, Line 14 (approx.), after the first paragraph, insert the text:
--STATEMENT REGARDING FEDERALLY FUNDED RESEARCH
This invention was made with government support under grant number AI073780 awarded by the National Institutes of Health. The government has certain rights in the invention.--

Signed and Sealed this
Ninth Day of April, 2019

Andrei Iancu
*Director of the United States Patent and Trademark Office*